US012708750B2

(12) United States Patent
Nguyen et al.

(10) Patent No.: US 12,708,750 B2
(45) Date of Patent: Aug. 18, 2026

(54) CORE-SHELL MICRONEEDLE PLATFORM FOR TRANSDERMAL AND PULSATILE DRUG/VACCINE DELIVERY AND METHOD OF MANUFACTURING THE SAME

(71) Applicant: University of Connecticut, Farmington, CT (US)

(72) Inventors: Thanh D. Nguyen, Vernon, CT (US); Khanh Tran, Farmington, CT (US)

(73) Assignee: University of Connecticut, Farmington, CT (US)

( * ) Notice: Subject to any disclaimer, the term of this patent is extended or adjusted under 35 U.S.C. 154(b) by 897 days.

(21) Appl. No.: 17/871,490

(22) Filed: Jul. 22, 2022

(65) Prior Publication Data

US 2022/0355089 A1 Nov. 10, 2022

Related U.S. Application Data

(62) Division of application No. 16/293,588, filed on Mar. 5, 2019, now Pat. No. 11,426,570.

(Continued)

(51) Int. Cl.

| | |
|---|---|
| ***A61M 37/00*** | (2006.01) |
| ***A61B 17/20*** | (2006.01) |

(Continued)

(52) U.S. Cl.

CPC ....... *A61M 37/0015* (2013.01); *A61B 17/205* (2013.01); *B29C 39/006* (2013.01); *B29C 39/026* (2013.01); *B29C 41/003* (2013.01); *B29C 43/003* (2013.01); *B29C 43/021* (2013.01); *B29C 43/32* (2013.01); *B29C 65/02* (2013.01); *A61M 2037/0023* (2013.01);

(Continued)

(58) Field of Classification Search

CPC ...... A61M 37/0015; A61M 2037/0023; A61M 2037/0046

See application file for complete search history.

(56) References Cited

U.S. PATENT DOCUMENTS

| | | |
|---|---|---|
| 4,438,773 A | 3/1984 | Letterio |
| 5,131,276 A | 7/1992 | Kibblewhite |

(Continued)

FOREIGN PATENT DOCUMENTS

| | | |
|---|---|---|
| CN | 102657914 B | 5/2015 |
| CN | 106109792 A | 11/2016 |

(Continued)

OTHER PUBLICATIONS

Curry et al., Supporting Information Appendix. Biodegradable piezoelectric force sensor. PNAS. Jan. 2018 pp. 1-33 (Year: 2018).

(Continued)

*Primary Examiner* — Emily L Schmidt

(74) *Attorney, Agent, or Firm* — Alix, Yale & Ristas, LLP

(57) ABSTRACT

A core-shell microneedle system and a method of manufacturing the microneedle system provides a pulsatile drug delivery system which is programmed to release drugs/vaccines at predictable times using biodegradable polymers and with controllable dosages. This microneedle system can be fully embedded into the skin and then release drugs/vaccines as sharp bursts in a timely manner, similar to multiple bolus injections.

11 Claims, 7 Drawing Sheets

Related U.S. Application Data

(60) Provisional application No. 62/638,758, filed on Mar. 5, 2018.

(51) Int. Cl.
*B29C 39/00* (2006.01)
*B29C 39/02* (2006.01)
*B29C 41/00* (2006.01)
*B29C 43/00* (2006.01)
*B29C 43/02* (2006.01)
*B29C 43/32* (2006.01)
*B29C 65/02* (2006.01)

(52) U.S. Cl.
CPC ................ *A61M 2037/003* (2013.01); *A61M 2037/0046* (2013.01); *A61M 2037/0053* (2013.01); *A61M 2037/0061* (2013.01); *B29C 43/02* (2013.01)

(56) References Cited

U.S. PATENT DOCUMENTS 5,246,013 A 9/1993 Frank et al.
5,287,331 A 2/1994 Schindel et al.
5,306,620 A 4/1994 Ginsberg et al.
5,443,495 A 8/1995 Buscemi et al.
5,498,499 A 3/1996 Flow et al.
5,512,600 A 4/1996 Mikos et al.
5,514,378 A 5/1996 Mikos et al.
5,678,565 A 10/1997 Sarvazyan
5,697,901 A 12/1997 Eriksson
5,794,023 A 8/1998 Hobbs et al.
5,827,198 A 10/1998 Kassal
5,891,191 A 4/1999 Stinson
6,142,948 A 11/2000 Toda
6,219,574 B1 4/2001 Cormier et al.
6,334,856 B1 1/2002 Allen et al.
6,447,887 B1 9/2002 Claus et al.
6,468,219 B1 10/2002 Njemanze
6,503,231 B1 1/2003 Prausnitz et al.
6,611,707 B1 8/2003 Prausnitz et al.
6,627,421 B1 9/2003 Unger et al.
6,835,377 B2 12/2004 Goldberg et al.
6,945,952 B2 9/2005 Kwon
7,001,372 B2 2/2006 Richter
7,184,826 B2 2/2007 Cormier et al.
7,332,197 B2 2/2008 Wood et al.
7,344,499 B1 3/2008 Prausnitz et al.
7,396,537 B1 7/2008 Krupnick et al.
7,578,954 B2 8/2009 Gartstein et al.
7,763,203 B2 7/2010 Arias et al.
7,879,093 B2 2/2011 Wei et al.
7,906,223 B2 3/2011 Rakow et al.
8,067,110 B2 11/2011 Rakow et al.
8,101,114 B2 1/2012 Park et al.
8,162,901 B2 4/2012 Gonnelli et al.
D659,820 S 5/2012 Abel et al.
8,267,889 B2 9/2012 Cantor et al.
8,301,262 B2 10/2012 Mi et al.
8,366,677 B2 2/2013 Kaspar et al.
8,469,936 B2 6/2013 Robinson et al.
8,551,391 B2 10/2013 Chang et al.
8,708,966 B2 4/2014 Allen et al.
8,798,932 B2 8/2014 Boyden et al.
8,821,446 B2 9/2014 Trautman et al.
8,834,423 B2 9/2014 Falo, Jr. et al.
8,911,749 B2 12/2014 Ghartey-Tagoe et al.
8,946,974 B2 2/2015 Yu et al.
8,955,515 B2 2/2015 Rakow et al.
9,040,087 B2 5/2015 Boyden et al.
9,050,053 B2 6/2015 Morgan
9,089,677 B2 7/2015 Soo et al.
9,114,238 B2 8/2015 Singh et al.
9,174,035 B2 11/2015 Ringsred et al.
9,192,655 B2 11/2015 Arinzeh et al.
9,289,925 B2 3/2016 Ferguson et al.
9,302,903 B2 4/2016 Park et al.
9,364,426 B2 6/2016 Gill et al.
9,381,680 B2 7/2016 Oh et al.
9,444,030 B2 9/2016 Wang et al.
9,452,280 B2 9/2016 Singh et al.
9,498,524 B2 11/2016 Ghartey-Tagoe et al.
9,517,205 B2 12/2016 O'Hagan et al.
9,527,257 B2 12/2016 Lipton et al.
9,675,789 B2 6/2017 Chen et al.
9,795,774 B2 10/2017 Takada et al.
9,846,091 B2 12/2017 Lu et al.
9,849,270 B2 12/2017 Stockholm
9,943,673 B2 4/2018 Kendall et al.
9,944,019 B2 4/2018 Falo, Jr. et al.
10,004,790 B2 6/2018 D'Souza
10,098,574 B1 10/2018 Kam
10,195,410 B2 2/2019 Jin
10,238,848 B2 3/2019 Singh et al.
10,245,421 B2 4/2019 Ross
10,265,511 B2 4/2019 McAllister et al.
10,292,831 B2 5/2019 Zellmer et al.
10,300,136 B2 5/2019 Jaklenec et al.
10,377,062 B2 8/2019 Kaspar et al.
10,384,045 B2 8/2019 Ding et al.
10,500,300 B2 12/2019 Dybe et al.
10,617,880 B2 4/2020 Zellmer et al.
10,624,865 B2 4/2020 Pathak
10,632,653 B2 4/2020 Niitsu et al.
10,668,260 B2 6/2020 Omachi et al.
10,710,011 B2 7/2020 Inoue et al.
10,792,857 B2 10/2020 Desimone et al.
10,821,275 B2 11/2020 Quan et al.
10,828,478 B2 11/2020 McAllister et al.
10,960,073 B2 3/2021 Jaklenec et al.
10,994,111 B2 5/2021 Quan et al.
11,045,433 B2 6/2021 Pathak
11,179,553 B2 11/2021 Kendall et al.
11,565,097 B2 1/2023 Bayramov et al.
11,590,330 B2 2/2023 McAllister et al.
11,724,079 B2 8/2023 McAllister et al.
11,744,927 B2 9/2023 Falo, Jr. et al.
11,975,069 B2 5/2024 Jaklenec et al.
11,998,712 B2 6/2024 Quan et al.
12,048,824 B2 7/2024 Quan et al.
12,090,295 B2 9/2024 Meliga et al.
2002/0081732 A1 6/2002 Bowlin et al.
2002/0082543 A1* 6/2002 Park .................. A61M 37/0015 604/20
2004/0015211 A1 1/2004 Nurmikko et al.
2004/0018226 A1 1/2004 Wnek et al.
2004/0028655 A1 2/2004 Nelson et al.
2005/0248547 A1 11/2005 Kent et al.
2005/0261631 A1 11/2005 Clarke et al.
2006/0043843 A1 3/2006 Sugiura et al.
2006/0050189 A1 3/2006 Ito et al.
2006/0107749 A1 5/2006 Liu et al.
2006/0190080 A1 8/2006 Danoff et al.
2006/0224237 A1 10/2006 Furst et al.
2007/0141106 A1 6/2007 Bonutti et al.
2007/0191761 A1 8/2007 Boone et al.
2007/0225631 A1 9/2007 Bowlin et al.
2007/0255422 A1 11/2007 Wei et al.
2007/0270738 A1 11/2007 Wu et al.
2007/0293912 A1 12/2007 Cowan et al.
2008/0009802 A1 1/2008 Lambino et al.
2008/0058633 A1 3/2008 Boyden et al.
2008/0269666 A1 10/2008 Wang et al.
2009/0030365 A1 1/2009 Tokumoto et al.
2009/0035446 A1 2/2009 Kwon
2009/0062723 A1 3/2009 Skiba
2009/0131905 A1 5/2009 Allen et al.
2009/0163965 A1 6/2009 Boyden et al.
2009/0182306 A1 7/2009 Lee et al.
2009/0192431 A1 7/2009 Horstmann et al.
2009/0280153 A1 11/2009 Hunter et al.
2010/0152644 A1 6/2010 Pesach et al.
2011/0028905 A1 2/2011 Takada
2011/0109204 A1 5/2011 Tajitsu et al.

(56) References Cited

U.S. PATENT DOCUMENTS

2011/0230747 A1 9/2011 Rogers et al.
2011/0242310 A1 10/2011 Beebe et al.
2012/0197155 A1 8/2012 Mattes et al.
2012/0226295 A1 9/2012 Jabbari
2012/0330250 A1* 12/2012 Kuwahara ......... A61M 37/0015 604/272
2013/0005708 A1 1/2013 Lalwani
2013/0041244 A1 2/2013 Woias et al.
2013/0086703 A1 4/2013 Maruyama et al.
2013/0140649 A1 6/2013 Rogers et al.
2013/0338632 A1* 12/2013 Kaplan ................. A61L 31/125 604/173
2014/0005606 A1 1/2014 Chen et al.
2014/0145365 A1 5/2014 Omenetto et al.
2014/0276378 A1 9/2014 Chen et al.
2014/0316333 A1 10/2014 Kwon
2014/0333184 A1 11/2014 Wang et al.
2015/0073551 A1 3/2015 Uehlin
2015/0134061 A1 5/2015 Friis et al.
2015/0165020 A1 6/2015 Jaklenec et al.
2016/0005951 A1 1/2016 Yoshida et al.
2016/0050750 A1 2/2016 Rogers et al.
2016/0067375 A1 3/2016 Holmes et al.
2016/0095599 A1 4/2016 Jose et al.
2016/0175408 A1 6/2016 Chang et al.
2016/0184571 A1 6/2016 Admati
2016/0184595 A1 6/2016 Hossainy
2016/0190427 A1 6/2016 Kim et al.
2016/0287668 A1 10/2016 Tankovich
2017/0020402 A1 1/2017 Rogers et al.
2017/0027168 A1 2/2017 Heath
2017/0080196 A1 3/2017 Lee et al.
2017/0179370 A1 6/2017 Kim et al.
2017/0189660 A1* 7/2017 Baek ........................ B05D 1/00
2017/0252546 A1 9/2017 Park et al.
2017/0258738 A1 9/2017 DeMuth et al.
2017/0268942 A1 9/2017 Pedder et al.
2017/0306295 A1 10/2017 Hazot et al.
2017/0368321 A1 12/2017 Baek
2018/0055643 A1 3/2018 Castro et al.
2018/0078498 A1 3/2018 Petersson et al.
2018/0140817 A1 5/2018 Spector
2018/0256905 A1 9/2018 Francia et al.
2018/0289616 A1 10/2018 Chen et al.
2018/0325806 A1 11/2018 Litvack et al.
2018/0344998 A1* 12/2018 Ono ........................ B29C 39/00
2019/0142318 A1 5/2019 Diebold et al.
2019/0209819 A1 7/2019 Ross
2019/0217071 A1 7/2019 Engel et al.
2019/0269895 A1 9/2019 Nguyen et al.
2019/0307697 A1 10/2019 Ma et al.
2019/0319181 A1 10/2019 Melandso et al.
2019/0328285 A1 10/2019 Liu
2019/0330771 A1 10/2019 Takumi et al.
2020/0009767 A1 1/2020 Li
2020/0093966 A1 3/2020 Rabolt et al.
2020/0276018 A1 9/2020 Nguyen et al.
2020/0276365 A1 9/2020 Nguyen et al.
2020/0282350 A1 9/2020 Inoue et al.
2020/0292206 A1 9/2020 Tamakura et al.
2020/0313066 A1 10/2020 Getman
2021/0031439 A1 2/2021 Desimone et al.
2021/0127998 A1 5/2021 Nguyen et al.
2021/0170152 A1 6/2021 Kendall et al.
2021/0178138 A1 6/2021 Gao et al.
2021/0275472 A1 9/2021 Pathak
2021/0276228 A1 9/2021 Shastry et al.
2021/0283387 A1 9/2021 Silbart et al.
2021/0378949 A1 12/2021 Nguyen et al.
2021/0379249 A1 12/2021 Nguyen et al.
2022/0096371 A1 3/2022 Nguyen et al.
2022/0176171 A1 6/2022 Nguyen et al.
2022/0249822 A1 8/2022 Karchin et al.
2023/0134250 A1 5/2023 Bayramov et al.
2023/0226334 A1 7/2023 McAllister et al.
2023/0278266 A1 9/2023 Kaspar et al.
2023/0311426 A1 10/2023 Falo, Jr. et al.
2023/0381478 A1 11/2023 McAllister et al.
2023/0398203 A1 12/2023 O'Hagan et al.
2024/0181047 A1 6/2024 Jaklenec et al.
2024/0238486 A1 7/2024 Falo, Jr.

FOREIGN PATENT DOCUMENTS

EP 0955359 B1 1/2009
EP 1993621 B1 8/2011
EP 1715915 B1 11/2012
EP 2482772 B1 10/2018
EP 3542740 A1 9/2019
IN 202041031484 A 7/2020
KR 101832716 B1 2/2018
RU 2082467 C1 6/1997
WO 2006055795 A1 5/2006
WO WO 2006057987 A1 6/2006
WO 2006101459 A1 9/2006
WO WO 2008085904 A1 7/2008
WO 2010124255 A2 10/2010
WO WO 2012103257 A2 8/2012
WO WO 2012127224 A1 9/2012
WO WO 2013101908 A1 7/2013
WO WO 2014143412 A8 11/2014
WO WO 2017003238 A1 1/2017
WO WO 2017011320 A1 1/2017
WO WO 2017139253 A1 8/2017
WO WO 2017151715 A1 9/2017
WO 2017191542 A1 11/2017
WO WO 2018017196 A1 1/2018
WO WO 2018089918 A1 5/2018
WO WO 2018114871 A1 6/2018
WO WO 2018170132 A1 9/2018
WO WO 2019025625 A1 2/2019
WO WO 2019094349 A1 5/2019
WO WO 2019143293 A1 7/2019
WO 2024059152 A2 3/2024

OTHER PUBLICATIONS

Amini et al., "Bone tissue engineering: recent advances and challenges," Critical Reviews™ in Biomedical Engineering, 2012, 40,(5):363-408.

Ando et al., "Film sensor device fabricated by a piezoelectric poly(L-lactic acid) film", 2012, Jpn J Appl Phys 51:09LD14.

Ando et al., "Pressure-sensitive touch panel based on piezoelectric poly (l-lactic acid) film", 2013, Jpn. J. Appl. Phys. 52:09KD17.

Anglen, "The clinical use of bone stimulators," Journal of the Southern Orthopaedic Association, 2002, 12, (2), 46-54.

Bauer et al., "Bone Graft Materials: An Overview of the Basic Science," Clinical orthopaedics and related research, 2000, 371, 10-27.

Bello et al., "Development of a smart pump for monitoring and controlling intraocular pressure", Ann Biomed Eng 45:990-1002, 2017.

Bos et al., "Resorbable poly(L-lactide) plates and screws for the fixation of zygomatic fractures", 1987, J Oral Maxillofac Surg, 45:751-753.

Boutry et al., "A sensitive and Biodegradable Pressure Sensor Array For Cardiovascular Monitoring", Advanced Materials, 27, 2015, pp. 6954-6961.

Bussemer et al., "Pulsatile drug-delivery systems," Crit Rev Ther Drug Syst., 2001, 18(5):433-458, Abstract.

Carpentier et al., "Clinical trial of blood-brain barrier disruption by pulsed ultrasound," Science translational medicine, 2016, 8(343):343re2, 9 pages.

Chee et al., "An investigation of array of piezoelectric transducer for raindrop energy harvesting application", 2016, IEEE Region Tenth Conference, pp. 3771-3774.

Chen et al., "Fully embeddable chitosan microneedles as a sustained release depot for intradermal vaccination," Biomaterials, 2013, 34(12):3077-3086.

(56) References Cited

OTHER PUBLICATIONS

Chiappini et al., "Biodegradable silicon nanoneedles delivering nucleic acids intracellularly induce localized in vivo neovascularization," Nature Materials, 2015, 14:532-539.
Cohen et al., "Totally implanted direct current stimulator as treatment for a nonunion in the foot," The Journal of foot and ankle surgery: official publication of the American College of Foot and Ankle Surgeons, 1993, 32, (4), 375-381.
Csafeglobal, The Cost of a Broken Vaccine Cold Chain Part Two, Financial Cost. <http://csafeglobal.com/the-cost-of-a-broken-vaccine-cold-chain-part-two-financial-cost-1> Sep. 17, 2014, 3 pages.
Curry et al., "Biodegradable piezoelectric force sensor," PNAS, 2018, 115(5):909-914.
Dagdeviren et al., "Recent progress in flexible and stretchable piezoelectric devices for mechanical energy harvesting, sensing and actuation," Extreme Mechanics Letters, 2016, 9(1):269-281.
Dai et al., "Electrospun emodin polyvinylpyrrolidone blended nanofibrous membrane: a novel medicated biomaterial for drug delivery and accelerated wound healing," Journal of Materials Science: Materials in Medicine, 2012, 23(11):2709-2716.
Demiray, "Electro-mechanical remodelling of bones," International Journal of Engineering Science, 1983, 21, (9), 1117-1126.
Di Mario et al., "Drug-eluting bioabsorbable magnesium stent", 2004, J Interv Cardiol., 17:391-395.
D'Lima et al. "Implantable sensor technology: measuring bone and joint biomechanics of daily life in vivo", Arthritis Research and Therapy, 2013, 15: 203.
European Patent Office Extended Search Report for Application No. 18767093.0 dated Nov. 27, 2020 (13 pages).
European Patent Office Partial Search Report for Application No. 19764864 dated Dec. 21, 2021 (12 pages).
Ewald et al., "Monitoring of vital signs for long-term survival of mice under anesthesia", 2011, Cold Spring Harb Protoc. 2011:pdb.prot5563.
Ferreira et al., "Bone Collagen Role in Piezoelectric Mediated Remineralization," Acta Microscopica, 2009, 18(3):278-286.
Fukada, "New Piezoelectric polymers" 1998, Jpn J Appl Phys 37:2775-2780.
Glazner et al., "Cost of vaccine administration among pediatric practices," Pediatrics, 2009, 124(Supplement 5):S492-S498.
Graf et al., "In Stimulation of bone growth by implanted FEP electrets and PVDF piezoelectric films," Proceedings 5th International Symposium on Electrets (ISE 5), Heidelberg, 1985, pp. 813-818.
Guo et al., "Measurements of piezoelectric coefficient d33 of lead zirconate titanate thin films using a mini force hammer", 2013, J Vib Accoust, 135:011003.
Habibovic, "Strategic directions in osteoinduction and biomimetics," Tissue Engineering Part A, 2017, 23, (23-24), 1295-1296.
International Preliminary Report on Patentability for Application No. PCT/US2018/022441 dated Sep. 17, 2019 (10 pages).
International Search Report and Written Opinion for Application No. PCT/US2018/022441 dated Aug. 1, 2018 (12 pages).
International Search Report and Written Opinion for Application No. PCT/US2019/020838 dated Jun. 26, 2019 (14 pages).
Jayson et al., "Intra-articular pressure in rheumatoid arthritis of the knee 3. Pressure changes during joint use", Ann Rheum Dis, 1970, 29:401-408.
Kang et al., "Bioresorbable silicon electronic sensors for the brain", Nature, 2016, 530:71-76.
Klosterhoff et al., "Implantable Sensors for Regenerative Medicine", Journal of Biomechanical Engineering, ASME Feb. 2017, vol. 139, 021009-1.
Laurencin et al., "Bone graft substitutes," Expert Review of Medical Devices, 2006, 3(1):49-57.
Laurencin et al., "Regenerative engineering," Science translational medicine, 2012, 4(160): 160ed9, 4 pages.
Laurencin et al., "Tissue engineering: orthopedic applications," Annual review of biomedical engineering, 1999, 1, (1), 19-46.
Lee et al., "Micromachined piezolectric force senors based on PZT thin films", 1996, IEEE Trans Ultrason Farroelectri Freq Control, 43:553-559.
Liu et al., "Design and development of three-dimensional scaffolds for tissue engineering", 2007, Chem Eng Res Des, 85:1051-1064.
Madlon-Kay et al., "Too many shots? Parent, nurse, and physician attitudes toward multiple simultaneous childhood vaccinations," Archives of Family Medicine, 1994, 3(7):610-13.
Maloney et al., "Intracranial pressure monitoring in acute liver failure: Institutional case series", 2016, Neurocrit Care 25:86-93.
Mchugh et al., Fabrication of fillable microparticles and other complex 3D microstructures, Science, 2017, 357(6356):1138-1142.
Mchugh et al., "Single-injection vaccines: Progress, challenges, and opportunities," Journal of Controlled Release, 2015, 219:596-609.
Meng et al., "A Hybrid Inductive-Ultrasonic Link for Wireless Power Transmission to Millimeter-Sized Biomedical Implats," IEEE Transactions on Circuits and Systems—II: Express Briefs, 2017, 64(10):1137-1141.
Minary-Jolandan et al., "Nanoscale characterization of isolated individual type I collagen fibrils: Polarization and piezoelectricity", 2009, Nanotechnology 20:085706.
Narayanan et al., "Poly (lactic acid)-based biomaterials for orthopaedic regenerative engineering," Advanced drug delivery reviews, 2016, 107, 247-276.
Nguyen et al., "Piezoelectric nanoribbons for monitoring cellular deformations," Nature Nanotechnology, 2012, 7:587-593.
Nguyen et al., "Wafter-scale nanopatterning and translation into high-performance piezoelectric nanowires", 2010, Nano Lett 10: 4595-4599.
Nguyen, et al., "Bionics in tissue engineering" 2017, Tissue Engineering for Artifical Organs, pp. 677-669.
Poeggel et al., "Optical Fibre Pressure Sensors in Medical Applications," Sensors, 2015, 15(7):17115-17148.
Qi et al., "Enhanced piezoelectricity and stretchability in energy harvesting devices fabricated from buckled PZT ribbons", 2011, Nano Lett. 11:1331-1336.
Qi et al., "Stretchable piezoelectric nanoribbons for biocompatible energy harvesting", Stretchable Electrionics, pp. 111-139.
Ramadan et al., "A review of piezoelectric polymers as functional materials for electromechanical transducers," Smart Materials and Structures 23, 2014, 033001.
Rolland et al., "Direct fabrication and harvesting of monodisperse, shape-specific nanobiomaterials," Journal of the American Chemical Society, 2005, 127(28):10096-10100.
Ru et al., "Dominant B-form of poly(l-lactic acid) obtained directly from melt under shear and pressure fields", 2016, Macromolecules 49:3826-3837.
Sanni et al., "Inductive and Ultrasonic Multi-Tier Interface for Low-Power, Deeply Implantable Medical Devices," IEEE Transactions on Biomedical Circuits and Systems, 2012, 6(4):297-308.
Sara Vanos et al., "Layerwise mechanics and finite element for the dynamic analysis of piezoelectric composite plates", 1997, Int J Solids Struct 34:359-378.
Sawano et al., "New design of actuator using shear piezoelectricity of a chiral polymer, and prototype device", 2010, Polym. Int. 59: 365-370.
Seol et al., "Hysteretic behavior of contact force response in triboelectric nanogenerator", 2017, Nano Energy 32:408-413.
Shende et al., Micro to nanoneedles: a trend of modernized transepidermal drug delivery system, Artificial Cells, Nanomedicine, and Biotechnology, 2017, 8 pages.
Simonelli et al., "Dissolution rates of high energy polyvinylpyrrolidone (PVP)-sulfathiazole coprecipitates," Journal of pharmaceutical sciences, 1969, 58(5):538-549.
Sinderby et al., "Diaphragm activation during exercise in chronic obstructive pulmonary disease", 2001, Am J Respir Crit Care Med, 163:1637-1641.
Soltman et al., "Inkjet-printed line morphologies and temperature control of the coffee ring effect," Langmuir, 2008, 24(5):2224-2231.
Sullivan et al., "Dissolving polymer microneedle patches for influenza vaccination," Nature medicine, 2010, 16(8):915-921.
Syuhei et al., "Sensing using piezoelectric chiral polymer fiber", 2012, Jpn. J. Appl. Phys. 51:09LD16.

(56) References Cited

OTHER PUBLICATIONS

Tajitsu et al., "Microactuators with piezoelectric polylactic acid fibers—toward the realizaation of tweezers for biological cells", 2004, Ferroelectrics 304:195-200.
Talmor et al., "Mechanical ventilation guided by esophageal pressure in acute lung injury", N. Engl. J Med., 2008, 359, 2095-2104.
Tanimoto et al., "Effect of helix inversion of poly(β-phenethyl l-aspartate) on macroscopic piezoelectricity," Japanese Journal of Applied Physics, 2014, 53(9S):09PC01.
Vaers, Vaccine Adverse Event Reporting System. <https://vaers.hhs.gov/data/index> webpage available as early as Oct. 9, 2009, 2 pages.
Xu et al., "Future of the particle replication in nonwetting templates (PR.INT) technology," Angewandte Chemie International Edition, 2013, 52(26):6580-6589.
Xu et al., "Improvements of thermal property and crystallization behavior of PLLA based multiblock copolymer by forming sterocomplex with PDLA oligomer", 2006, Polymer (Guildf), 47:3922-3928.
Yoshida et al., "High piezoelectric performance of poly (lactic acid) film manufactured by solid state extrusion", 2014, Jpn. J. Appl. Phys. 53:09PC02.
Yoshida et al., "Piezolectric motion of multilayer film with alternate rows of optical isomers of chiral polymer film", 2011, Jpn J Appl Phys 50:09ND13.
Yu et al., "Oral fast-dissolving drug delivery membranes prepared from electrospun polyvinylpyrrolidone ultrafine fibers," Nanotechnology, 2009, 20(5):055104, 9 pages.
Zhang et al., "Piezoelectric polymer multilayer on flexible substrate for energy harvesting," IEEE Transactions on Ultrasonics, Ferroelectrics, and Frequency Control, 2013, 60(9):2013-2020.
Zheng et al., "Biodegradable triboelectric nongenerator as a lifetime designed implantable power source", 2016, Sci Adv 2:e1501478.
Zi et al., "Triboelectric-pyroelectric-piezoelectric hybrid cell for high-efficiency energy-harvesting and self-powered sensing", Adv Mater 27:2340-2347, 2015.
Abcam. ELISA kit for MCP-1. https://www.abcam.com/rat-mcp1-elisa-kit-ab219045.html. Accessed Aug. 22, 2022 (5 pages).
Abcam. ELISA kit for TNF-alpha. https://www.abcam.com/rat-tnf-alpha-elisa-kit-ab236712.html. Accessed Aug. 22, 2022 (5 pages).
AFPRO Filters. Pm1: The Most Hazardous Kind of Particulate Matter. https://web.archive.org/web/20200609213853/https://www.afprofilters.com/pm1-airfilter/, Jun. 9, 2020, (4 pages).
Ager, D. J. et al. Stability of aspirin in solid mixtures. Journal of pharmaceutical sciences 1986, 75, (1), 97-101.
Alemdaroğlu, C.; et al. An investigation on burn wound healing in rats with chitosan gel formulation containing epidermal growth factor. Burns 2006, 32, (3), 319-327.
Alneami AQ, et al. Effect of Electrical Current Stimulation on Pseudomonas Aeruginosa Growth. Journal of Physics: Conference Series. 2018;1003:012112.
Amirnasr, E. et al. Basis Weight Uniformity Analysis in Nonwovens. The Journal of The Textile Institute 2014, 105 (4), 444-453.
Ando et al., "New human machine interface devices using a piezoelectric poly(L-lactic acid) film" in 2013 IEEE International Symposium on the Applications of Ferroelectric and Workshop on the Piezoresponse Force Microscopy (ISAF/PFM) (IEEE, 2013), pp. 236-239.
Arakha M, et al. The effects of interfacial potential on antimicrobial propensity of ZnO nanoparticle. Scientific Reports. 2015;5(1):9578.
Asadi MR, et al. Bacterial Inhibition by Electrical Stimulation. Advances in Wound Care. 2013;3(2):91-97.
Atkins et al. Raman spectroscopy of blood and blood components. Appl. Spectrosc. 71, 767-793 (2017).
Babu, R. et al. Assessment of skin irritation and molecular responses in rat skin exposed to nonane, dodecane and tetradecane. Toxicology letters 2004, 153, (2), 255-266.
Bai, Y.; et al. Washable Multilayer Triboelectric Air Filter for Efficient Particulate Matter Pm2. 5 Removal. Advanced Functional Materials 2018, 28 (15), 1706680.
Baker, B., et al. Electrical stimulation of articular cartilage regeneration. Annals of the New York Academy of Sciences 238, 491-499 (1974).
Banerjee J, et al. Silver-zinc redox-coupled electroceutical wound dressing disrupts bacterial biofilm. PLoS One. 2015;10(3):e0119531-e0119531.
Barbour, K. E.; et al., Prevalence of doctor-diagnosed arthritis and arthritis-attributable activity limitation—United States, 2010-2012. MMWR. Morbidity and mortality weekly report 2013, 62, (44), 869-873.
Barbour, K. E.; et al., Vital signs: prevalence of doctor-diagnosed arthritis and arthritis-attributable activity limitation—United States, 2013-2015. MMWR. Morbidity and mortality weekly report 2017, 66, (9), 246-253.
Barki KG, et al. Electric Field Based Dressing Disrupts Mixed-Species Bacterial Biofilm Infection and Restores Functional Wound Healing. Ann Surg. 2019;269(4).
Barton, N. J.; et al., Demonstration of a novel technique to quantitatively assess inflammatory mediators and cells in rat knee joints. Journal of Inflammation 2007, 4, (1), 13.
Bastaki, S. M.; et al. Effect of Aspirin and ibuprofen either alone or in combination on gastric mucosa and bleeding time and on serum prostaglandin E 2 and thromboxane A 2 levels in the anaesthetized rats in vivo. Molecular and cellular biochemistry 2018, 438, (1-2), 25-34.
Baur D, Gladstone BP, Burkert F, Carrara E, Foschi F, Dobele S, Tacconelli E: Effect of antibiotic stewardship on the incidence of infection and colonisation with antibiotic-resistant bacteria and *Clostridium difficile* infection: a systematic review and meta-analysis. Lancet Infect Dis 2017, 17(9):990-1001.
BCC Research—Global Markets for Drug-Device Combinations, Jan. 2015. PHM045D.
Beaudet J, Tulman ER, Pflaum K, Liao X, Kutish GF, Szczepanek SM, Silbart LK, Geary SJ: Transcriptional Profiling of the Chicken Tracheal Response to Virulent Mycoplasma gallisepticum Strain Rlow. Infect Immun 2017, 85(10).
Bergsma JE, et al. Late degradation tissue response to poly(l-lactide) bone plates and screws. Biomaterials. 1995;16(1):25-31.
Besinis, A.; et al. Antibacterial activity and biofilm inhibition by surface modified titanium alloy medical implants following application of silver, titanium dioxide and hydroxyapatite nanocoatings. Nanotoxicology 2017, 11, (3), 327-338.
Bir SC, et al. Control of angiogenesis dictated by picomolar superoxide levels. Free Radic Biol Med. 2013;63:135-142.
Blake KM, Carrigan SO, Issekutz AC, Stadnyk AW: Neutrophils migrate across intestinal epithelium using beta2 integrin (CD11b/CD18)-independent mechanisms. Clin Exp Immunol 2004, 136(2):262-268.
Bloomberg News. Mask Mandates by Nation: Most Still Await a Breath of Fresh Air. https://www.bloomberg.com/news/articles/2021-05-14/mask-mandates-by-nation-most-still-await-a-breath-of-fresh-air. May 14, 2021 (9 pages).
Boks NP, et al. Forces involved in bacterial adhesion to hydrophilic and hydrophobic surfaces. Microbiology. 2008;154(Pt 10):3122-3133.
Bose, S.; et al. A review on advances of sustained release drug delivery system. Int. Res. J. Pharm 2013, 4, 1-4.
Boster Bio. ELISA kit for IL-1 alpha. https://www.bosterbio.com/rat-il-1-alpha-picokine-trade-elisa-kit-ek0390-boster.html#bs_references. Jul. 1, 2013. Accessed on Aug. 22, 2022. (8 pages).
Bottino, M. C. et al. in Biomaterials for Oral and Craniomaxillofacial Applications vol. 17 90-100 (Karger Publishers, 2015).
Boutry et al., A stretchable and biodegradable strain and pressure sensor for orthopaedic application. Nat. Electron. 1, 314-321 (2018).
Boutry et al., Biodegradable and flexible arterial-pulse sensor for the wireless monitoring of blood flow. Nat. Biomed. Eng. 3, 47-57 (2019).
Bronaugh, R. L.; et al., Differences in permeability of rat skin related to sex and body site. J. Soc. Cosmet. Chem 1983, 34, (12), 127-135.
Brooks, J. T.; et al., Effectiveness of Mask Wearing to Control Community Spread of Sars-Cov-2. Jama 2021, 325 (10), 998-999.

(56) References Cited

OTHER PUBLICATIONS

Brune, K.; et al. Recent Insight into the Mechanism of Gastrointestinal Tract Ulceration. Scandinavian Journal of Rheumatology 1987, 16, (sup65), 135-140.
Byrne, J. D.; et al., Injection Molded Autoclavable, Scalable, Conformable (Imasc) System for Aerosol-Based Protection: A Prospective Single-Arm Feasibility Study. BMJ open 2020, 10 (7), e039120.
Caballe-Serrano, J. et al. On the search of the ideal barrier membrane for guided bone regeneration. Journal of clinical and experimental dentistry 10, e477 (2018).
Cadavid, A. P., Aspirin: the mechanism of action revisited in the context of pregnancy complications. Frontiers in immunology 2017, 8, 261.
Campbell, C. L. et al. Aspirin dose for the prevention of cardiovascular disease: a systematic review. Jama 2007, 297, (18), 2018-2024.
Carvalho, E. O., et al. "Tailoring bacteria response by piezoelectric stimulation." ACS applied materials & interfaces 11.30 (2019): 27297-27305.
Caspani, M. Delta Variant Pushes US Cases Hospitalizations 6 Month High. Aug. 9, 2021. https://web.archive.org/web/20210809174911/https://www.reuters.com/world/us/delta-variant-pushes-us-cases-hospitalizations-6-month-high-2021-08-09/ (12 pages).
CDC. Antibiotic resistance threats in the United States, 2019. US Department of Health and Human Services. 2019 (150 pages).
CDC. Implementing Filtering Facepiece Respirator (Ffr) Reuse, Including Reuse after Decontamination, When There Are Known Shortages of N95 Respirators. https://www.cdc.gov/coronavirus/2019-ncov/hcp/ppe-strategy/decontamination-reuse-respirators.html, Oct. 19, 2020, (10 pages).
CDC. Periodontal Disease. <https://www.cdc.gov/oralhealth/conditions/periodontal-disease.html> (Jul. 10, 2013) (3 pages).
CDC. Personal Protective Equipment: Questions and Answers. https://www.cdc.gov/coronavirus/2019-ncov/hcp/respirator-use-faq.html (Apr. 9, 2021) (6 pages).
Chang et al., Biodegradable electronic systems in 3D, heterogeneously integrated formats. Adv. Mater. 30, 1704955 (2018).
Chatterjee, A.; et al., In vitro and in vivo comparison of dermal irritancy of jet fuel exposure using EpiDerm™(EPI-200) cultured human skin and hairless rats. Toxicology letters 2006, 167, (2), 85-94.
Chen, C.-C.; et al. Aerosol Penetration through Surgical Masks. American journal of infection control 1992, 20 (4), 177-184.
Chen, M.-C. et al. Implantable polymeric microneedles with phototriggerable properties as a patient-controlled transdermal analgesia system. Journal of Materials Chemistry B 2017, 5, (3), 496-503.
Cheng, Y.; et al. Face Masks Effectively Limit the Probability of Sars-Cov-2 Transmission. Science 2021 1439-1443.
Choi, S.; et al. Biodegradable, Efficient, and Breathable Multi-Use Face Mask Filter. Advanced Science 2021, 8 (6), 2003155.
Chorsi MT, et al. Piezoelectric Biomaterials for Sensors and Actuators. Advanced Materials. 2019;31(1):1802084.
Chu et al., "Piezoelectric stimulation by ultrasound facilitates chondrogenesis of mesenchymal stem cells", J Acoustical Society of American, 2020, vol. 148, No. 1, pp. EL58-EL64.
Chu, D. K.; et al. Physical Distancing, Face Masks, and Eye Protection to Prevent Person-to-Person Transmission of Sars-Cov-2 and Covid-19: A Systematic Review and Meta-Analysis. The lancet 2020, 395 (10242), 1973-1987.
Chu, J.; et al. Thinking Green: Modelling Respirator Reuse Strategies to Reduce Cost and Waste. BMJ open 2021, 11 (7), e048687.
Clearfield, D. S., et al. Osteochondral Differentiation of Fluorescent Multireporter Cells on Zonally-Organized Biomaterials. Tissue Engineering Part A 25, 468-486 (2019).
Cohen, A. J.; et al. Estimates and 25-Year Trends of the Global Burden of Disease Attributable to Ambient Air Pollution: An Analysis of Data from the Global Burden of Diseases Study 2015. The Lancet 2017, 389 (10082), 1907-1918.
Combe, R.; et al. The monosodium iodoacetate model of osteoarthritis: a model of chronic nociceptive pain in rats? Neuroscience letters 2004, 370, (2-3), 236-240.
Cooper MA, et al. Fix the antibiotics pipeline. Nature. 2011;472(7341):32-32.
Creech et al., "Prevention of Recurrent Staphylococcal Skin Infections," Infect Dis Clin North Am. Sep. 2015; 29(3): 429-464.
Crofford, L. J., Use of NSAIDs in treating patients with arthritis. Arthritis research & therapy 2013, 15, (3), S2 (10 pages).
Crone S, et al. A novel in vitro wound biofilm model used to evaluate low-frequency ultrasonic-assisted wound debridement. J Wound Care. 2015;24(2):64-72.
Cui, et al. Study on a piezoelectric micropump for the controlled drug delivery system. Microfluid. Nanofluidics 3, 377-390 (2007).
Curdy, C. et al. Piroxicam delivery into human stratum corneum in vivo: iontophoresis versus passive diffusion. Journal of Controlled Release 2001, 76, (1-2), 73-79.
Curry EJ, et al. Biodegradable nanofiber-based piezoelectric transducer. Proceedings of the National Academy of Sciences. 2020;117(1):214-220.
Curry, E. J.; et al. 3D nano- and micro-patterning of biomaterials for controlled drug delivery. Therapeutic Delivery 2016.
Da Silva et al., Biocompatibility, biodegradation and excretion of polylactic acid (PLA) in medical implants and theranostic systems. Chem. Eng. J. 340, 9-14 (2018).
Daeschlein G, et al. Antibacterial activity of positive and negative polarity low-voltage pulsed current (LVPC) on six typical Gram-positive and Gram-negative bacterial pathogens of chronic wounds. Wound Repair Regen. 2007;15(3):399-403.
Dagdeviren C, et al. Conformable amplified lead zirconate titanate sensors with enhanced piezoelectric response for cutaneous pressure monitoring. Nature Communications. 2014;5(1):4496.
Dagdeviren C, et al. Conformal piezoelectric energy harvesting and storage from motions of the heart, lung, and diaphragm. Proceedings of the National Academy of Sciences. 2014;111(5):1927.
Das, R. et al. Biodegradable Nanofiber Bone-Tissue Scaffold as Remotely-Controlled and Self-Powering Electrical Stimulator. Nano Energy 2020, 105028.
Davidson, C. I.; et al. Airborne Particulate Matter and Human Health: A Review. Aerosol Science and Technology 2005, 39 (8), 737-749.
Degenhart et al., Histological evaluation of a chronically-implanted electrocorticographic electrode grid in a non-human primate. 13, 046019 (2016).
Deleo et al., "Reemergence of antibiotic-resistant *Staphylococcus aureus* in the genomics era," JCL, 2009, 119, 2464-2474.
Deleo FR, Diep BA, Otto M: Host defense and pathogenesis in Staphylococcus aureus infections. Infect Dis Clin North Am 2009, 23(1):17-34.
Derakhshandeh H, et al. A Wirelessly Controlled Smart Bandage with 3D-Printed Miniaturized Needle Arrays. Adv Funct Mater. 2020;30(13):1905544.
Desai, T. A.; et al., Nanoporous implants for controlled drug delivery. In BioMEMS and Biomedical Nanotechnology, Springer: 2006; pp. 263-286.
Dimitroulas, T.; et al. In Biologic drugs as analgesics for the management of osteoarthritis, Seminars in arthritis and rheumatism, 2017; Elsevier: pp. 687-691.
Dixon, W. J. et al. A method for obtaining and analyzing sensitivity data. Journal of the American Statistical Association 1948, 43, (241), 109-126.
Dominguez, C. A. et al. Sex differences in the development of localized and spread mechanical hypersensitivity in rats after injury to the infraorbital or sciatic nerves to create a model for neuropathic pain. Gender medicine 2009, 6, 225-234.
Dong P-T, et al. Photolysis of Staphyloxanthin in Methicillin-Resistant *Staphylococcus aureus* Potentiates Killing by Reactive Oxygen Species. Advanced Science. 2019;6(11):1900030.
Donnelly, R. F.; et al. Hydrogel-forming microneedle arrays for enhanced transdermal drug delivery. Advanced functional materials 2012, 22, (23), 4879-4890.

(56) References Cited

OTHER PUBLICATIONS

Draize, J. H. et al. Methods for the study of irritation and toxicity of substances applied topically to the skin and mucous membranes. Journal of pharmacology and Experimental Therapeutics 1944, 82, (3), 377-390.
Dwyer DJ, et al. Antibiotics induce redox-related physiological alterations as part of their lethality. Proceedings of the National Academy of Sciences of the United States of America. 2014;111(20):E2100-2109.
Englander L, et al. Nitric oxide nanoparticle technology: a novel antimicrobial agent in the context of current treatment of skin and soft tissue infection. J Clin Aesthet Dermatol. 2010;3(6):45-50.
Eppley BL, et al. Degradation characteristics of PLLA-PGA bone fixation devices. The Journal of craniofacial surgery. 1997;8(2):116-120.
Esposito S, et al. Antimicrobial Treatment of *Staphylococcus aureus* in Patients With Cystic Fibrosis. Front Pharmacol. 2019;10:849-849.
European Patent Office Extended Search Report for Application No. 19764864 dated Mar. 22, 2022 (11 pages).
Farah et al. Physical and mechanical properties of PLA, and their functions in widespread applications—a comprehensive review. Adv. Drug Deliv. Rev. 107, 367-392 (2016).
FDA. N95 Respirators, Surgical Masks, and Face Masks. https://www.fda.gov/medical-devices/personal-protective-equipment-infection-control/n95-respirators-surgical-masks-face-masks-and-barrier-face-coverings Last updated Jul. 19, 2022 (6 pages).
Feng, Y. et al. Engineering Spherical Lead Zirconate Titanate to Explore the Essence of Piezo-Catalysis. Nano Energy 2017, 40, 481-486.
Feng, Y.; et al. Self-Powered Electrostatic Filter with Enhanced Photocatalytic Degradation of Formaldehyde Based on Built-in Triboelectric Nanogenerators. ACS nano 2017, 11 (12), 12411-12418.
Formenti, D.; et al. Thermal imaging of exercise-associated skin temperature changes in trained and untrained female subjects. Annals of biomedical engineering 2013, 41, (4), 863-871.
Fosslien, E., Adverse effects of nonsteroidal anti-inflammatory drugs on the gastrointestinal system. Annals of Clinical & Laboratory Science 1998, 28, (2), 67-81.
Foti JJ, et al. Oxidation of the Guanine Nucleotide Pool Underlies Cell Death by Bactericidal Antibiotics. Science. 2012;336(6079):315-319.
Freeman J, et al. Comparison of the efficacy of ramoplanin and vancomycin in both in vitro and in vivo models of clindamycin-induced *Clostridium difficile* infection. J Antimicrob Chemother. 2005;56(4):717-725.
Friebe, M.; et al. Synovial distribution of "systemically" administered acetylsalicylic acid in the isolated perfused equine distal limb. BMC veterinary research 2013, 9, (1), 56.
Frim, J. et al. Body composition and skin temperature variation. Journal of Applied Physiology 1990, 68, (2), 540-543.
Fu, C.-H. J. et al. Method for determination of aspirin and salicylic acid in rat whole blood by high pressure liquid chromatography. Analytical Letters 1985, 18, (3), 269-277.
Gabriel D, et al. A photo-triggered layered surface coating producing reactive oxygen species. Biomaterials. 2013;34(38):9763-9769.
Gao, Q., et al. Ultrasound Stimulation of Different Dental Stem Cell Populations: Role of Mitogen-activated Protein Kinase Signaling. J. Endod. 42, 2016, 425-431.
Garland MJ(1), Migalska K, Mahmood TM, Singh TR, Woolfson AD, Donnelly RF. Microneedle arrays as medical devices for enhanced transdermal drug delivery Expert Rev Med Devices. Jul. 2011;8(4):459-82.
Gentile, P. et al. An overview of poly (lactic-co-glycolic) acid (PLGA)-based biomaterials for bone tissue engineering. International journal of molecular sciences 2014, 15, (3), 3640-3659.
Gibaldi, M. et al. Bioavailability of aspirin from commercial suppositories. Journal of pharmaceutical sciences 1975, 64, (6), 1064-1066.
Gohil, S. V. et al. Spatially controlled rhBMP-2 mediated calvarial bone formation in a transgenic mouse model. International journal of biological macromolecules 2018, 106, 1159-1165.
Golabchi et al., Melatonin improves quality and longevity of chronic neural recording. 180, 225-239 (2018).
Gordon CP, Williams P, Chan WC: Attenuating *Staphylococcus aureus* virulence gene regulation: a medicinal chemistry perspective. J Med Chem 2013, 56(4):1389-1404.
Gottlieb, H. E.; et al. Nmr Chemical Shifts of Common Laboratory Solvents as Trace Impurities. Journal of Organic Chemistry 1997, 62 (21), 7512-7515.
Grant SS, et al. Eradication of bacterial persisters with antibiotic-generated hydroxyl radicals. Proceedings of the National Academy of Sciences. 2012; 109(30):12147.
Grassi, M.; et al. Mathematical modelling and controlled drug delivery: matrix systems. Current drug delivery 2005, 2, (1), 97-116.
Gu, G. Q. et al. Triboelectric Nanogenerator Enhanced Nanofiber Air Filters for Efficient Particulate Matter Removal. Acs Nano 2017, 11 (6), 6211-6217.
Guerin et al., Control of piezoelectricity in amino acids by supramolecular packing. Nat. Mater. 17, 180-186 (2018).
Guo, H.; et al. A pure zinc membrane with degradability and osteogenesis promotion for guided bone regeneration: in vitro and in vivo studies. Acta Biomater. 2020, 396-409.
Gurung, D. et al. Transient temperature distribution in human dermal part with protective layer at low atmospheric temperature. International Journal of Biomathematics 2010, 3, (04), 439-451.
Gustafsson, M. et al. Pain, coping and analgesic medication usage in rheumatoid arthritis patients. Patient education and counseling 1999, 37, (1), 33-41.
Gutarowska, B., et al. "PLA nonwovens modified with poly (dimethylaminoethyl methacrylate) as antimicrobial filter materials for workplaces." Textile Research Journal 85.10 (2015): 1083-1094.
Haddadin et al., "Methicillin resistant *Staphylococcus aureus* (MRSA) in the intensive care unit," Postgraduate Medical Journal 2002; 78:385-392.
Hasuike A, et al. In vivo bone regenerative effect of low-intensity pulsed ultrasound in rat calvarial defects. Oral Surgery, Oral Medicine, Oral Pathology, Oral Radiology, and Endodontology. 2011;111(1):e12-e20.
Hauert AB, Martinelli S, Marone C, Niggli V: Differentiated HL-60 cells are a valid model system for the analysis of human neutrophil migration and chemotaxis. Int J Biochem Cell Biol 2002, 34(7):838-854.
He, M. et al. Intradermal implantable PLGA microneedles for etonogestrel sustained release. Journal of Pharmaceutical Sciences 2020, 1958-1966.
He, Z. et al. An overview of hydrogel-based intra-articular drug delivery for the treatment of osteoarthritis. Colloids and Surfaces B: Biointerfaces 2017, 154, 33-39.
Hickey, D.J., et al. Electrophoretic deposition of MgO nanoparticles imparts antibacterial properties to poly-L-lactic acid for orthopedic applications. Journal of Biomedical Materials Research Part A, 2017, 105(11), 3136-3147.
Hong K-S, et al. Piezoelectrochemical Effect: A New Mechanism for Azo Dye Decolorization in Aqueous Solution through Vibrating Piezoelectric Microfibers. The Journal of Physical Chemistry C. 2012;116(24):13045-13051.
Horodyckid et al., Safe long-term repeated disruption of the blood-brain barrier using an implantable ultrasound device: A multiparametric study in a primate model. J. Neurosurg. 126, 1351-1361 (2017).
Hossain, E.; et al. Recharging and Rejuvenation of Decontaminated N95 Masks. Physics of Fluids 2020, 32 (9), 093304.
Howard, J.; et al., An Evidence Review of Face Masks against Covid-19. Proceedings of the National Academy of Sciences 2021, 118 (4).
Hu H, et al. Stretchable ultrasonic transducer arrays for three-dimensional imaging on complex surfaces. Science Advances. 2018;4(3):eaar3979.
Huang, X.; et al. On the importance and mechanisms of burst release in matrix-controlled drug delivery systems. Journal of controlled release 2001, 73, (2-3), 121-136.

(56) References Cited

OTHER PUBLICATIONS

Huij, et al. Photo-Disassembly of Membrane Microdomains Revives Conventional Antibiotics against MRSA. Advanced Science. 2020;7(6):1903117.
Iati, M. More Experts Now Recommend Medical Masks. Good Ones Are Hard to Find. Feb. 2, 2021. https://www.washingtonpost.com/health/2021/02/02/medical-mask-shortage/ (4 pages).
IDATA Reasearch. 2017 US Dental Barrier Membrane Market Driven by Increased Use of Resorbable Membranes. https://idataresearch.com/2017-US-dental-barrier-membrane-market-driven-increased-use-resorbable-membranes/. Nov. 10, 2017. (6 pages).
Idbaih et al., Safety and feasibility of repeated and transient blood-brain barrier disruption by pulsed ultrasound in patients with recurrent glioblastoma. Clin. Cancer Res. 25, 3793-3801 (2019).
Ikada et al. Enhancement of bone formation by drawn poly(L-lactide). J. Biomed. Mater. Res. 30, 553-558 (1996).
Indian Office Action for Application 202037042930 dated Jun. 20, 2022 (6 pages).
Infection Control Today, "New Research Estimates MRSA Infections Cost U.S. Hospitals $3.2 Billion to $4.2 Billion Annually," <https://www.infectioncontroltoday.com/view/new-research-estimates-mrsa-infections-cost-us-hospitals-32-billion-42-billion-annually> dated May 16, 2005.
Institute of Medicine of the National Academies. Characteristics of Respirators and Medical Masks. In Reusability of Facemasks During an Influenza Pandemic: Facing the Flu, 2006; pp. 22-42.
International Preliminary Report on Patentability for Application No. PCT/US2021/021677 dated Sep. 6, 2022 (11 pages).
International Search Report and Written Opinion for Application No. PCT/US21/53887 dated Jan. 28, 2022 (14 pages).
Jacobi, U. et al. Porcine ear skin: an in vitro model for human skin. Skin Research and Technology 2007, 13, (1), 19-24.
Ji, W. et al. Incorporation of stromal cell-derived factor-1α in PCL/gelatin electrospun membranes for guided bone regeneration. Biomaterials 34, 735-745 (2013).
Jin Y, Li M, Shang Y, Liu L, Shen X, Lv Z, Hao Z, Duan J, Wu Y, Chen C et al: Sub-Inhibitory Concentrations of Mupirocin Strongly Inhibit Alpha-Toxin Production in High-Level Mupirocin-Resistant MRSA by Down-Regulating agr, saeRS, and sarA. Front Microbiol 2018, 9:993.
Jung, Y.-s. et al. Thermo-sensitive injectable hydrogel based on the physical mixing of hyaluronic acid and Pluronic F-127 for sustained NSAID delivery. Carbohydrate polymers 2017, 156, 403-408.
Jüni, P.; et al. Intra-articular corticosteroid for knee osteoarthritis. Cochrane Database of Systematic Reviews 2015, (10) (81 pages).
Kalali Y, Haghighat S, Mahdavi M: Passive immunotherapy with specific IgG fraction against autolysin: Analogous protectivity in the MRSA infection with antibiotic therapy. Immunol Lett 2019, 212:125-131.
Kaushik, S. et al. Lack of pain associated with microfabricated microneedles. Anesthesia & Analgesia 2001, 92, (2), 502-504.
Kean, T.; et al. Biodegradation, Biodistribution and Toxicity of Chitosan. Advanced drug delivery reviews 2010, 62 (1), 3-11.
Kern, H., et al. Recovery of long-term denervated human muscles induced by electrical stimulation. Muscle & nerve 31, 98-101 (2005).
Khalid, B.; et al., Direct Blow-Spinning of Nanofibers on a Window Screen for Highly Efficient Pm2. 5 Removal. Nano letters 2017, 17 (2), 1140-1148.
Khanal, M.; et al. Injectable nanocomposite analgesic delivery system for musculoskeletal pain management. Acta biomaterialia 2018, 74, 280-290.
Kim, D.-H. et al. Sustained release of dexamethasone from hydrophilic matrices using PLGA nanoparticles for neural drug delivery. Biomaterials 2006, 27, (15), 3031-3037.
Kinoshita, N. et al. Noninvasive localized delivery of Herceptin to the mouse brain by MRI-guided focused ultrasound-induced bloodbrain barrier disruption. Proc. Natl. Acad. Sci. U.S.A. 103, 11719-11723 (2006).
Klein et al., "National Costs Associated With Methicillin-Susceptible and Methicillin-Resistant *Staphylococcus aureus* Hospitalizations in the United States, 2010-2014," Clinical Infectious Diseases, vol. 68, Issue 1, Jan. 1, 2019, pp. 22-28.
Kloth, L. C. Electrical stimulation for wound healing: a review of evidence from in vitro studies, animal experiments, and clinical trials. The international journal of lower extremity wounds 4, 23-44 (2005).
Kobayashi, et al. Label-free imaging of melanoma with confocal photothermal microscopy: Differentiation between malignant and benign tissue. Bioeng. 5, 67 (2018) (18 pages).
Kohanski MA, et al. A Common Mechanism of Cellular Death Induced by Bactericidal Antibiotics. Cell. 2007;130(5):797-810.
Kozai et al., Chronic tissue response to carboxymethyl cellulose based dissolvable insertion needle for ultra-small neural probes. 35, 9255-9268 (2014).
Krasowska A A, et al. How microorganisms use hydrophobicity and what does this mean for human needs? Front Cell Infect Microbiol. 2014;4:112-112.
Kullenberg, B. et al. Intraarticular corticosteroid injection: pain relief in osteoarthritis of the hip? The Journal of rheumatology 2004, 31, (11), 2265-2268.
Latimer, J. M. et al. Microwave Oven Irradiation as a Method for Bacterial Decontamination in a Clinical Microbiology Laboratory. Journal of Clinical Microbiology 1977, 6 (4), 340-342.
Laurencin, C. T.; et al. Delivery of small molecules for bone regenerative engineering: preclinical studies and potential clinical applications. Drug discovery today 2014, 19, (6), 794-800.
Lausen M, Pedersen MS, Rahman NSK, Holm-Nielsen LT, Farah FYM, Christiansen G, Birkelund S: Opsonophagocytosis of Chlamydia pneumoniae by Human Monocytes and Neutrophils. Infect Immun 2020, 88(7).
Leatherby, L. As Covid Cases Rise All over U.S., Lower Vaccination Rates Point to Worse Outcomes. Jul. 31, 2021. https://www.nytimes.com/interactive/2021/07/31/US/covid-delta-cases-deaths.html?action=click&module=Spotlight&pgtype=Homepage (3 pages).
Lee et al., Lactic acid assisted fabrication of bioactive three-dimensional PLLA/β-TCP fibrous scaffold for biomedical application. Chem. Eng. J. 347, 771-781 (2018).
Lee, et al. Piezoelectric properties of electrospun poly(L-lactic acid) nanofiber web. Mater. Lett. 148, 58-62 (2015).
Leung, L. et al. Comparison of morphology and mechanical properties of PLGA bioscaffolds. Biomedical Materials 2008, 3, (2), 025006.
Lewin et al., Free serum haemoglobin is associated with brain atrophy in secondary progressive multiple sclerosis. Wellcome Open Res. 1, 10 (2016) (23 pages).
Lewitus, S. et al. The Effect of Nanoclays on the Properties of PLLA-modified Polymers Part 1: Mechanical and Thermal Properties. Journal of Polymers and the Environment 14, 171-177 (2006).
Li J, et al. Evaluation of Ultrasound-Induced Damage to *Escherichia coli* and *Staphylococcus aureus* by Flow Cytometry and Transmission Electron Microscopy. Appl Environ Microbiol. 2016;82(6):1828-1837.
Liz, et al. Using Positively Charged Magnetic Nanoparticles to Capture Bacteria at Ultralow Concentration. Nanoscale Research Letters. 2019;14(1):195 (8 pages).
Li, C. et al. Dual-mode operation of flexible piezoelectric polymer diaphragm for intracranial pressure measurement. Appl. Phys. Lett. 96, 053502 (2010).
Li, H. et al. Enhancing the Mechanical Properties of Electrospun Nanofiber Mats through Controllable Welding at the Cross Points. Macromolecular rapid communications 2017, 38 (9), 1600723.
Li, N.; et al. A Work Group Report on Ultrafine Particles (American Academy of Allergy, Asthma & Immunology): Why Ambient Ultrafine and Engineered Nanoparticles Should Receive Special Attention for Possible Adverse Health Outcomes in Human Subjects. Journal of Allergy and Clinical Immunology 2016, 138 (2), 386-396.
Li, P. et al. Air Filtration in the Free Molecular Flow Regime: A Review of High-Efficiency Particulate Air Filters Based on Carbon Nanotubes. Small 2014, 10 (22), 4543-4561.

(56) References Cited

OTHER PUBLICATIONS

Li, P. et al. Apatite formation induced by silica gel in a simulated body fluid. Journal of the American Ceramic Society 1992, 75, (8), 2094-2097.
Li, Q. et al. Involvement of the spinal NALP1 inflammasome in neuropathic pain and aspirin-triggered-15-epi-lipoxin A4 induced analgesia. Neuroscience 2013, 254, 230-240.
Li, W. et al. Rapidly separable microneedle patch for the sustained release of a contraceptive. Nature Biomedical Engineering 2019, 3, (3), 220-229.
Li, W.; et al. Long-acting reversible contraception by effervescent microneedle patch. Science advances 2019, 5, (11), eaaw8145.
Liao, L.; et al. Can N95 Respirators Be Reused after Disinfection? How Many Times? ACS nano 2020, 14 (5), 6348-6356.
Liu, C.; et al. Transparent Air Filter for High-Efficiency Pm 2.5 Capture. Nature communications 2015, 6 (1), 1-9.
Liu, G. et al. Self-Powered Electrostatic Adsorption Face Mask Based on a Triboelectric Nanogenerator. ACS applied materials & interfaces 2018, 10 (8), 7126-7133.
Liu, H. et al. High-Performance Pm0. 3 Air Filters Using Self-Polarized Electret Nanofiber/Nets. Advanced Functional Materials 2020, 30 (13), 1909554.
Liu, X. et al. A biodegradable multifunctional nanofibrous membrane for periodontal tissue regeneration. Acta Biomater. 2020, 108, 207-222.
Liu, Z.; et al. Understanding the Factors Involved in Determining the Bioburdens of Surgical Masks. Annals of translational medicine 2019, 7 (23).
Lo, K. et al. Small-molecule based musculoskeletal regenerative engineering. Trends in biotechnology 2014, 32, (2), 74-81.
Lobritz MA, et al. Antibiotic efficacy is linked to bacterial cellular respiration. Proceedings of the National Academy of Sciences of the United States of America. 2015;112(27):8173-8180.
Lokuta MA, Nuzzi PA, Huttenlocher A: Analysis of neutrophil polarization and chemotaxis. Methods Mol Biol 2007, 412:211-229.
Long Y, et al. Effective Wound Healing Enabled by Discrete Alternative Electric Fields from Wearable Nanogenerators. ACS Nano. 2018;12(12):12533-12540.
Lops, C.; et al. Sonophotocatalytic Degradation Mechanisms of Rhodamine B Dye Via Radicals Generation by Micro-and Nano-Particles of Zno. Applied Catalysis B: Environmental 2019, 243, 629-640.
Lu, W.-C. et al. Effect of magnesium on the osteogenesis of normal human osteoblasts. Magnes. Res. 30, 42-52 (2017).
Lu, X.; et al. Theoretical analysis of calcium phosphate precipitation in simulated body fluid. Biomaterials 2005, 26, (10), 1097-1108.
Ludwig, The velocity of sound through tissues and the acoustic impedance of tissues. The journal of the acoustical society of America 22, 862-866 (1950).
Lundgren, D., et al. "The use of a new bioresorbable barrier for guided bone regeneration in connection with implant installation. Case reports." Clinical Oral Implants Research 5.3 (1994): 177-184.
Luque-Agudo V, et al. Aging of Solvent-Casting PLA-Mg Hydrophobic Films: Impact on Bacterial Adhesion and Viability. Coatings. 2019;9(12) 814.
Luzuriaga MA(1), Berry DR, Reagan JC, Smaldone RA, Gassensmith JJ. Biodegradable 3D printed polymer microneedles for transdermal drug delivery. Lab Chip. Apr. 17, 2018;18(8):1223-1230.
Lv, D.; et al. Ecofriendly Electrospun Membranes Loaded with Visible-Light-Responding Nanoparticles for Multifunctional Usages: Highly Efficient Air Filtration, Dye Scavenging, and Bactericidal Activity. ACS applied materials & interfaces 2019, 11 (13), 12880-12889.
Mahdavi, A. et al. Particle Loading Time and Humidity Effects on the Efficiency of an N95 Filtering Facepiece Respirator Model under Constant and Inhalation Cyclic Flows. Annals of Occupational Hygiene 2015, 59 (5), 629-640.
Manoukian, M. A. C. et al. Topical administration of ibuprofen for injured athletes: considerations, formulations, and comparison to oral delivery. Sports medicine-open 2017, 3, (1), 36, 1-9.
Marzoli, F. et al. Long-lasting, antinociceptive effects of pH-sensitive niosomes loaded with ibuprofen in acute and chronic models of pain. Pharmaceutics 2019, 11, (2), 62, 1-12.
Mcallister DV(1), Wang PM, Davis SP, Park JH, Canatella PJ, Allen MG, Prausnitz MR. Microfabricated needles for transdermal delivery of macromolecules and nanoparticles: fabrication methods and transport studies. Proc Natl Acad Sci U S A. Nov. 25, 2003;100(24):13755-60.
Mccrudden, M. T. et al. Design and physicochemical characterisation of novel dissolving polymeric microneedle arrays for transdermal delivery of high dose, low molecular weight drugs. Journal of Controlled Release 2014, 180, 71-80.
Mcdannold, et al. MRI-guided targeted blood-brain barrier disruption with focused ultrasound: Histological findings in rabbits. Ultrasound Med. Biol. 31, 1527-1537 (2005).
Meylan S, et al. Targeting Antibiotic Tolerance, Pathogen by Pathogen. Cell. 2018;172(6):1228-1238.
Middleton, J. C.; Tipton, A. J., Synthetic Biodegradable Polymers as Orthopedic Devices. Biomaterials 2000, 21 (23), 2335-2346.
Mihai MM, et al. Nanomaterials for Wound Healing and Infection Control. Materials (Basel). 2019;12(13):2176.
Millius A, Weiner OD: Chemotaxis in neutrophil-like HL-60 cells. Methods Mol Biol 2009, 571:167-177.
Moga, K. A. et al. Rapidly-dissolvable microneedle patches via a highly scalable and reproducible soft lithography approach. Advanced Materials 2013, 25, (36), 5060-5066.
Mohseni et al., "Gellan gel comprising short PVDF based-nanofibers: The effect of piezoelectric nanofiber on the mechanical and electrical behavior," Materialstoday Communications, vol. 26, Mar. 2021, 101785.
Monsen T, et al. In Vitro Effect of Ultrasound on Bacteria and Suggested Protocol for Sonication and Diagnosis of Prosthetic Infections. J Clin Microbiol. 2009;47(8):2496-2501.
Montgomery CP, Boyle-Vavra S, Daum RS: Importance of the global regulators Agr and SaeRS in the pathogenesis of CA-MRSA USA300 infection. PLoS One 2010, 5(12):e15177.
Morel CM, et al. Stoking the antibiotic pipeline. BMJ. 2010;340:1115-1118.
Nair, L. S.; et al. Polymers as biomaterials for tissue engineering and controlled drug delivery. In Tissue engineering I, Springer: 2005; pp. 47-90.
Najdovski, L. et al. The Killing Activity of Microwaves on Some Non-Sporogenic and Sporogenic Medically Important Bacterial Strains. Journal of Hospital Infection 1991, 19 (4), 239-247.
Nasajpour, A. et al. A multifunctional polymeric periodontal membrane with osteogenic and antibacterial characteristics. Adv. Funct. Mater. 28, 1703437 (2018).
Nazir, M. A. Prevalence of periodontal disease, its association with systemic diseases and prevention. International journal of health sciences 11, 72 (2017), 72-80.
Neely RM, et al. Recent advances in neural dust: towards a neural interface platform. Current Opinion in Neurobiology. 2018;50:64-71.
Nguyen, "A novel injectable piezoelectric hydrogel for osteoarthritis treatment," NIH Project No. 1R21AR074645-01, Award notice date: Apr. 23, 2019, Project Start Date: Jun. 1, 2019 <https://reporter.nih.gov/project-details/9651964> (3 pages).
Nicosia, A., et al. "Air filtration and antimicrobial capabilities of electrospun PLA/PHB containing ionic liquid." Separation and Purification Technology 154 (2015): 154-160.
Nielsen A, Mansson M, Bojer MS, Gram L, Larsen TO, Novick RP, Frees D, Frokiaer H, Ingmer H: Solonamide B inhibits quorum sensing and reduces *Staphylococcus aureus* mediated killing of human neutrophils. PLoS One 2014, 9(1):e84992.
Noguchi, Y. Why N95 Masks Are Stil in Short Supply in the U.S. https://www.npr.org/sections/health-shots/2021/01/27/960336778/why-n95-masks-are-still-inshort-supply-in-the-u-s, Jan. 27, 2021 (17 pages).

(56) References Cited

OTHER PUBLICATIONS

Norman, J. J.; et al. Microneedle patches: usability and acceptability for self-vaccination against influenza. Vaccine 2014, 32, (16), 1856-1862.
Novotny et al. Molybdenum intake influences molybdenum kinetics in men. J. Nutr. 137, 37-42 (2007).
O'Dowd et al., "Face Masks and Respirators in the Fight Against the COVID-19 Pandemic: A Review of Current Materials, Advances and Future Perspectives," Materials 2020, 13(15), 3363.
Olatunji, O.; et al. Microneedle-assisted transdermal delivery of acetylsalicylic acid (aspirin) from biopolymer films extracted from fish scales. Polymer Bulletin 2018, 75, (9), 4103-4115.
Omidinia-Anarkoli, A.; et al. An Injectable Hybrid Hydrogel with Oriented Short Fibers Induces Unidirectional Growth of Functional Nerve Cells. Small 2017, 13, (36).
O'Riordan K, Lee JC: *Staphylococcus aureus* capsular polysaccharides. Clin Microbiol Rev 2004, 17(1):218-234.
Padilla F, et al. Stimulation of bone repair with ultrasound: A review of the possible mechanic effects. Ultrasonics. 2014;54(5):1125-1145.
Panieri E, et al. ROS signaling and redox biology in endothelial cells. Cell Mol Life Sci. 2015;72(17):3281-3303.
Pankey GA, et al. Clinical relevance of bacteriostatic versus bactericidal mechanisms of action in the treatment of Gram-positive bacterial infections. Clin Infect Dis. 2004;38(6):864-870.
Park, J.-H. et al. Biodegradable polymer microneedles: fabrication, mechanics and transdermal drug delivery. Journal of controlled release 2005, 104, (1), 51-66.
Parlet CP, Kavanaugh JS, Crosby HA, Raja HA, El-Elimat T, Todd DA, Pearce CJ, Cech NB, Oberlies NH, Horswill AR: Apicidin Attenuates MRSA Virulence through Quorum-Sensing Inhibition and Enhanced Host Defense. Cell Rep 2019, 27(1):187-198 e186.
Patel et al., "Development of a Sonically Powered Biodegradable Nanogenerator for Bone Regeneration", 2019, University of Connecticut, 46 pages.
Pathak, R. K. et al. A nanoparticle cocktail: temporal release of predefined drug combinations. Journal of the American Chemical Society 2015, 137, (26), 8324-8327.
Patrick, J.; et al. A randomized trial to assess the pharmacodynamics and pharmacokinetics of a single dose of an extended-release aspirin formulation. Postgraduate medicine 2015, 127, (6), 573-580.
Paul, et al. Novel 3D analysis of Claudin-5 reveals significant endothelial heterogeneity among CNS microvessels. 86, 1-10 (2013).
Pavel A, et al. Prophylactic Antibiotics in Clean Orthopaedic Surgery. JBJS. 1974;56(4):777-782.
Pelletier, J.-P.; et al. In Efficacy and safety of oral NSAIDs and analgesics in the management of osteoarthritis: Evidence from real-life setting trials and surveys, Seminars in arthritis and rheumatism, 2016; Elsevier: pp. S22-S27.
Peltoniemi et al. SR-PLLA and SRPGA miniscrews: Biodegradation and tissue reactions in the calvarium and dura mater. J. Craniomaxillofac. Surg. 27, 42-50 (1999).
Peng, X., et al. "A breathable, biodegradable, antibacterial, and self-powered electronic skin based on all-nanofiber triboelectric nanogenerators." Science Advances 6.26 (2020): eaba9624.
Peterson RV, et al. The effect of frequency and power density on the ultrasonically-enhanced killing of biofilm-sequestered *Escherichia coli*. Colloids and Surfaces B: Biointerfaces. 2000; 17(4):219-227.
Prausnitz, M. R. Engineering microneedle patches for vaccination and drug delivery to skin. Annual review of chemical and biomolecular engineering 2017, 8, 177-200.
Pressmeddelande, "Microneedle Drug Delivery Systems Market 2018 Segmentation, Demand, Growth, Trend, Opportunity and Forecast to 2023," My News Desk, <https://www.mynewsdesk.com/se/probe-way/pressreleases/microneedle-drug-delivery-systems-market-2018-segmentation-demand-growth-trend-opportunity-and-forecast-to-2023-2672909> dated Sep. 3, 2018.
Prokuski L. Prophylactic Antibiotics in Orthopaedic Surgery. JAAOS—Journal of the American Academy of Orthopaedic Surgeons. 2008; 16(5):283-293.
Qian, Y. et al. Performance of N95 Respirators: Filtration Efficiency for Airborne Microbial and Inert Particles. American Industrial Hygiene Association Journal 1998, 59 (2), 128-132.
Qiu, Y. et al. Enhancement of skin permeation of docetaxel: a novel approach combining microneedle and elastic liposomes. Journal of Controlled Release 2008, 129, (2), 144-150.
Queck SY, Jameson-Lee M, Villaruz AE, Bach TH, Khan BA, Sturdevant DE, Ricklefs SM, Li M, Otto M: RNAIII-independent target gene control by the agr quorum-sensing system: insight into the evolution of virulence regulation in *Staphylococcus aureus*. Mol Cell 2008, 32(1):150-158.
Quinn, H. L. et al. Design of a dissolving microneedle platform for transdermal delivery of a fixed-dose combination of cardiovascular drugs. Journal of pharmaceutical sciences 2015, 104, (10), 3490-3500.
Ratajska, M. et al. Studies on the Biodegradation of Chitosan in an Aqueous Medium. Fibres & Textiles in Eastern Europe 2003, (3 (42)), 75--79.
Raynor, P. C. et al. The Long-Term Performance of Electrically Charged Filters in a Ventilation System. Journal of occupational and environmental hygiene 2004, 1 (7), 463-471.
Resistance WHO-TICCIoA: No time to wait: Securing the future from drug-resistant infections. In.; 2019. 28 pages.
Rigby KM, DeLeo FR: Neutrophils in innate host defense against *Staphylococcus aureus* infections. Semin Immunopathol 2012, 34(2):237-259.
Riggin, C. N.; et al. Intra-articular tibiofemoral injection of a nonsteroidal anti-inflammatory drug has No. detrimental effects on joint mechanics in a rat model. Journal of Orthopaedic Research 2014, 32, (11), 1512-1519.
Ripolin, A.; et al. Successful application of large microneedle patches by human volunteers. International journal of pharmaceutics 2017, 521, (1-2), 92-101.
Rizzello L, et al. Nanotechnology tools for antibacterial materials. Nanomedicine (Lond). 2013;8(5):807-821.
Roberts, M. S. et al. Percutaneous absorption of topically applied NSAIDS and other compounds: role of solute properties, skin physiology and delivery systems. Inflammopharmacology 1999, 7, (4), 339.
Robertson JMC, et al. A comparison of the effectiveness of TiO2 photocatalysis and UVA photolysis for the destruction of three pathogenic micro-organisms. Journal of Photochemistry and Photobiology A: Chemistry. 2005;175(1):51-56.
Rohrer, M. D. et al. Microwave Sterilization. Journal of the American Dental Association (1939) 1985, 110 (2), 194-198.
Roy S, et al. Disposable Patterned Electroceutical Dressing (PED-10) Is Safe for Treatment of Open Clinical Chronic Wounds. Advances in Wound Care. 2019;8(4):149-159.
Runyan CM, et al. Low-frequency ultrasound increases outer membrane permeability of Pseudomonas aeruginosa. The Journal of General and Applied Microbiology. 2006;52(5):295-301.
Ruparelia JP, et al. Strain specificity in antimicrobial activity of silver and copper nanoparticles. Acta Biomater. 2008;4(3):707-716.
Russell, R., Non-steroidal anti-inflammatory drugs and gastrointestinal damage—problems and solutions. Postgraduate medical journal 2001, 77, (904), 82-88.
Sadorsky, P., The Effect of Urbanization and Industrialization on Energy Use in Emerging Economies: Implications for Sustainable Development. American Journal of Economics and Sociology 2014, 73 (2), 392-409.
Salomonir R, et al. Antibacterial effect of silver nanoparticles in Pseudomonas aeruginosa. Nanotechnol Sci Appl. 2017;10:115-121.
Santora, M. et al. Covid Updates: Known Global Tool Reaches 200 Millions Virus Infections. Aug. 4, 2021. https://web.archive.org/web/20210804234532/https://www.nytimes.com/live/2021/08/04/world/covid-delta-variant-vaccine (21 pages).
Schlesinger, E. et al. Polycaprolactone thin-film drug delivery systems: empirical and predictive models for device design. Materials Science and Engineering: C 2015, 57, 232-239.
Schlesinger, E.; et al. A tunable, biodegradable, thin-film polymer device as a long-acting implant delivering tenofovir alafenamide fumarate for HIV pre-exposure prophylaxis. Pharmaceutical research 2016, 33, (7), 1649-1656.

(56) References Cited

OTHER PUBLICATIONS

Schmook, F. P.; et al. Comparison of human skin or epidermis models with human and animal skin in in-vitro percutaneous absorption. International journal of pharmaceutics 2001, 215, (1-2), 51-56.
Schutze GE, Hall MA, Baker CJ, Edwards MS: Role of neutrophil receptors in opsonophagocytosis of coagulase-negative staphylococci. Infect Immun 1991, 59(8):2573-2578.
Sencadas et al., Local piezoelectric activity of single poly(L-lactic acid) (PLLA) microfibers. Appl. Phys. A 109, 51-55 (2012).
Seth AK, et al. Noncontact, low-frequency ultrasound as an effective therapy against Pseudomonas aeruginosa-infected biofilm wounds. Wound Repair Regen. 2013;21(2):266-274.
Shah SR, et al. Evolving strategies for preventing biofilm on implantable materials. Materials Today. 2013;16(5):177-182.
Shah, S.; et al. Controversies and advances in non-steroidal anti-inflammatory drug (NSAID) analgesia in chronic pain management. Postgraduate medical journal 2012, 88, (1036), 73-78.
Shalumon KT, et al. Sodium alginate/poly(vinyl alcohol)/nano ZnO composite nanofibers for antibacterial wound dressings. Int J Biol Macromol. 2011;49(3):247-254.
Sheets, D.; et al. An Apparatus for Rapid and Nondestructive Comparison of Masks and Respirators. Review of Scientific Instruments 2020, 91 (11), 114101.
Shim, J.-H. et al. Efficacy of rhBMP-2 loaded PCL/PLGA/β-TCP guided bone regeneration membrane fabricated by 3D printing technology for reconstruction of calvaria defects in rabbit. Biomedical materials 9, 065006 (2014) (9 pages).
Shokri, J.; et al. Swellable elementary osmotic pump (SEOP): an effective device for delivery of poorly water-soluble drugs. European Journal of Pharmaceutics and Biopharmaceutics 2008, 68, (2), 289-297.
Shrivastava S, et al. Characterization of enhanced antibacterial effects of novel silver nanoparticles. Nanotechnology. 2007;18(22):225103 (9 pages).
Shuai et al., "Surface modification enhances interfacial bonding in PLLA/MgO bone scaffold," Materials Science and Engineering: C, vol. 108, Mar. 2020, 110486.
Shuai, C. et al. nMgO-incorporated PLLA bone scaffolds: Enhanced crystallinity and neutralized acidic products. Materials & Design 174, 107801 (2019).
Silva, E.; et al. Pdlla Honeycomb-Like Scaffolds with a High Loading of Superhydrophilic Graphene/Multi-Walled Carbon Nanotubes Promote Osteoblast in Vitro Functions and Guided in Vivo Bone Regeneration. Materials Science and Engineering: C 2017, 73, 31-39.
Sinatra, R. S.; et al. Efficacy and safety of single and repeated administration of 1 gram intravenous acetaminophen injection (paracetamol) for pain management after major orthopedic surgery. Anesthesiology: The Journal of the American Society of Anesthesiologists 2005, 102, (4), 822-831.
Smith et al. Direct observation of shear piezoelectricity in poly-L-lactic acid nanowires. APL Mater. 5, 074105 (2017) (8 pages).
Starr MB, et al. Coupling of piezoelectric effect with electrochemical processes. Nano Energy. 2015; 14:296-311.
Stokes, A.; et al. The contribution of obesity to prescription opioid use in the United States. Pain 2019, 160, (10), 2255.
Subbiahdoss G, et al. Magnetic targeting of surface-modified superparamagnetic iron oxide nanoparticles yields antibacterial efficacy against biofilms of gentamicin-resistant staphylococci. Acta Biomater. 2012;8(6):2047-2055.
Sultana et al., Human skin interactive self-powered wearable piezoelectric bio-eskin by electrospun poly-L-lactic acid nanofibers for non-invasive physiological signal monitoring. J. Mater. Chem. B 5, 7352-7359 (2017).
Sutton et al., "Hospital-, Health Care-, and Community-Acquired MRSA: Estimates From California Hospitals, 2013," <https://www.hcup-us.ahrq.gov/reports/statbriefs/sb212-MRSA-Hospital-Stays-California-2013.jsp> dated Oct. 2016.
Szablowski, et al. Acoustically targeted chemogenetics for the non-invasive control of neural circuits. Nat. Biomed. Eng. 2, 475-484 (2018).
Taguchi, V. et al. Determination of drug stability in aspirin tablet formulations by high-pressure liquid chromatography. Journal of pharmaceutical sciences 1981, 70, (1), 64-67.
Tajitsu et al. Novel tweezers for biological cells using piezoelectric polylactic acid fibers. Ferroelectrics 320, 133-139 (2005).
Tajitsu, Y. Fundamental study on improvement of piezoelectricity of poly(ι-lactic acid) and its application to film actuators. IEEE Trans. Ultrason. Ferroelectr. Freq. Control 60, 1625-1629 (2013).
Takeuchi, H.; et al. Influence of skin thickness on the in vitro permeabilities of drugs through Sprague-Dawley rat or Yucatan micropig skin. Biological and Pharmaceutical Bulletin 2012, 35, (2), 192-202.
Tams J, et al. Poly(l-lactide) bone plates and screws for internal fixation of mandibular swing osteotomies. Int J Oral Maxillofac Surg. 1996;25(1):20-24.
Tan, et al. Studies on Thermal Decomposition Mechanism and Kinetics of Aspirin [J]. Acta Physico-chimica Sinica 2004, 1m 50-54. With English Abstract.
Tan, G., et al. "Surface-selective preferential production of reactive oxygen species on piezoelectric ceramics for bacterial killing." ACS applied materials & interfaces 8.37 (2016): 24306-24309.
Tao H, et al. Silk-based resorbable electronic devices for remotely controlled therapy and in vivo infection abatement. Proceedings of the National Academy of Sciences. 2014;111(49):17385.
Tezel A, et al. Topical Delivery of Anti-sense Oligonucleotides Using Low-Frequency Sonophoresis. Pharm Res. 2004;21(12):2219-2225.
Thakur, R. R. S.; et al. Microneedle-mediated intrascleral delivery of in situ forming thermoresponsive implants for sustained ocular drug delivery. Journal of Pharmacy and Pharmacology 2014, 66, (4), 584-595.
Thamma Vongsa V, Kim HK, Missiakas D, Schneewind O: Staphylococcal manipulation of host immune responses. Nat Rev Microbiol 2015, 13(9):529-543.
Thermofisher Scientific. Residual Solvent Analysis Information. Jul. 14, 2019. https://web.archive.org/web/20190714025617/https://www.thermofisher.com/us/en/home/industrial/pharma-biopharma/pharma-biopharma-learning-center/pharmaceutical-qa-qc-information/residual-solvent-analysis-information.html (6 pages).
Timin, A. S., et al. "Multifunctional scaffolds with improved antimicrobial properties and osteogenicity based on piezoelectric electrospun fibers decorated with bioactive composite microcapsules." ACS applied materials & interfaces 10.41 (2018): 34849-34868.
Tong SY, Davis JS, Eichenberger E, Holland TL, Fowler VG, Jr.: *Staphylococcus aureus* infections: epidemiology, pathophysiology, clinical manifestations, and management. Clin Microbiol Rev 2015, 28(3):603-661.
Tran, K. T.; et al. Lithography-based methods to manufacture biomaterials at small scales. Journal of Science: Advanced Materials and Devices 2017, 2, (1), 1-14.
Tucho, G. T.; et al., Universal Use of Face Masks and Related Challenges During Covid-19 in Developing Countries. Risk Management and Healthcare Policy 2021, 14, 511.
Ueki, H.; et al. Effectiveness of Face Masks in Preventing Airborne Transmission of Sars-Cov-2. MSphere 2020, 5 (5), e00637-20.
Ummadi, S.; et al. Overview on controlled release dosage form. System 2013, 7, (8), 51-60.
Valentini, R. F., et al. Electrically charged polymeric substrates enhance nerve fibre outgrowth in vitro. Biomaterials 13, 183-190 (1992).
Van Acker H, et al. The Role of Reactive Oxygen Species in Antibiotic-Mediated Killing of Bacteria. Trends in Microbiology. 2017;25(6):456-466.
Varrone JJ, et al. Passive immunization with anti-glucosaminidase monoclonal antibodies protects mice from implant-associated osteomyelitis by mediating opsonophagocytosis of *Staphylococcus aureus* megaclusters. J Orthop Res 2014, 32(10):1389-1396.
Varrone JJ, Li D, Daiss JL, Schwarz EM: Anti-Glucosaminidase Monoclonal Antibodies as a Passive Immunization for Methicillin-

(56) References Cited

OTHER PUBLICATIONS

Resistant *Staphylococcus aureus* (MRSA) Orthopaedic Infections. Bonekey Osteovision 2011, 8:187-194.
Vykhodtseva, et al. Progress and problems in the application of focused ultrasound for blood-brain barrier disruption. Ultrasonics 48, 279-296 (2008).
Vysakh et al., "A Comparative Analysis of Community Acquired and Hospital Acquired Methicillin Resistant *Staphylococcus aureus*," J Clin Diagn Res. Jul. 2013; 7(7): 1339-1342.
Walmsley, A. et al. Ultrasound in dentistry. Part 2—periodontology and endodontics. J. Dent. 20, 11-17 (1992).
Walsh C. Molecular mechanisms that confer antibacterial drug resistance. Nature. 2000;406(6797):775-781.
Wang F, Gao W, Thamphiwatana S, Luk BT, Angsantikul P, Zhang Q, Hu CM, Fang RH, Copp JA, Pornpattananangkul D et al: Hydrogel Retaining Toxin-Absorbing Nanosponges for Local Treatment of Methicillin-Resistant *Staphylococcus aureus* Infection. Adv Mater 2015, 27(22):3437-3443.
Wang Y, et al. Piezo-catalysis for nondestructive tooth whitening. Nature Communications. 2020;11(1):1328.
Wang, C. et al. Enhanced cancer immunotherapy by microneedle patch-assisted delivery of anti-PD1 antibody. Nano letters 2016, 16, (4), 2334-2340.
Wang, C. et al. Silk Nanofibers as High Efficient and Lightweight Air Filter. Nano Research 2016, 9 (9), 2590-2597.
Wang, N. et al. Tunable Fabrication of Three-Dimensional Polyamide-66 Nano-Fiber/Nets for High Efficiency Fine Particulate Filtration. Journal of Materials Chemistry 2012, 22 (4), 1445-1452.
Wang, P. et al. Ultrasmall Barium Titanate Nanoparticles for Highly Efficient Hypoxic Tumor Therapy Via Ultrasound Triggered Piezocatalysis and Water Splitting. ACS nano 2021, 11326-11340.
Wang, S. et al. Controlled release of levonorgestrel from biodegradable poly (D, L-lactide-co-glycolide) microspheres: in vitro and in vivo studies. International journal of pharmaceutics 2005, 301, (1-2), 217-225.
Wang, S. et al. Electret Polyvinylidene Fluoride Nanofibers Hybridized by Polytetrafluoroethylene Nanoparticles for High-Efficiency Air Filtration. ACS applied materials & interfaces 2016, 8 (36), 23985-23994.
Wang, Z. et al. Porous Bead-on-String Poly (Lactic Acid) Fibrous Membranes for Air Filtration. Journal of colloid and interface science 2015, 441, 121-129.
Wang, Z.-F. et al. Aspirin-triggered Lipoxin A4 attenuates mechanical allodynia in association with inhibiting spinal JAK2/STAT3 signaling in neuropathic pain in rats. Neuroscience 2014, 273, 65-78.
Ward AR, et al. Comparison of Heating of Nonliving Soft Tissue produced by 45 kHz and 1 MHz Frequency Ultrasound Machines. J Orthop Sports Phys Ther. 1996;23(4):258-266.
Wartzek, et al. Triboelectricity in capacitive biopotential measurements. IEEE Trans. Biomed. Eng. 58, 1268-1277 (2011).
WHO, "New report calls for urgent action to avert antimicrobial resistance crisis," <https://www.who.int/news/item/29-04-2019-new-report-calls-for-urgent-action-to-avert-antimicrobial-resistance-crisis> dated Apr. 29, 2019.
WHO. Coronavirus Disease (Covid-19) Advice for the Public: When and How to Use Masks. https://www.who.int/emergencies/diseases/novel-coronavirus-2019/advice-for-public/when-andhow-to-use-masks (Updated Dec. 2021) (12 pages).
WHO. Shortage of Personal Protective Equipment Endangering Health Workers Worldwide. https://www.who.int/news/item/03-03-2020-shortage-of-personal-protective-equipment-endangering-health-workers-worldwide. Mar. 3, 2020 (3 pages).
Wiese, A. D.; et al. Opioid analgesics and the risk of serious infections among patients with rheumatoid arthritis: a self-controlled case series study. Arthritis & rheumatology 2016, 68, (2), 323-331.
Witzleb et al. Exposure to chromium, cobalt and molybdenum from metal-on-metal total hip replacement and hip resurfacing arthroplasty. Acta Orthop. 77, 697-705 (2006).
Woltjer et al. (2016) "Optimization of piezo-MEMS layout for a bladder monitor" in 2016 IEEE International Ultrasonics Symposium (IUS) (IEEE, 2016), pp. 1-4.
Wu, S. et al. Surface Modification of Pure Magnesium Mesh for Guided Bone Regeneration: In Vivo Evaluation of Rat Calvarial Defect. Materials 12, 2684 (2019).
Wynn, R. F. et al. A small proportion of mesenchymal stem cells strongly expresses functionally active CXCR4 receptor capable of promoting migration to bone marrow. Blood 104, 2643-2645 (2004).
Xin et al., A Site-Specific Integrated Col2. 3GFP Reporter Identifies Osteoblasts Within Mineralized Tissue Formed In Vivo by Human Embryonic Stem Cells. Stem cells translational medicine 3, 1125-1137 (2014).
Xiong, Z.-C. et al. Flexible Hydroxyapatite Ultralong Nanowire-Based Paper for Highly Efficient and Multifunctional Air Filtration. Journal of Materials Chemistry A 2017, 5 (33), 17482-17491.
Xu X, et al. Strong vibration-catalysis of ZnO nanorods for dye wastewater decolorization via piezo-electro-chemical coupling. Chemosphere. 2018;193:1143-1148.
Xu, E. G.; et al.Preventing Masks from Becoming the Next Plastic Problem. Frontiers of environmental science & engineering 2021, 15 (6), 125.
Yang, M.; et al. Is Pm1 Similar to Pm2. 5? A New Insight into the Association of Pm1 and Pm2. 5 with Children's Lung Function. Environment International 2020, 145, 106092.
Yoshimoto, I. et al. Development of layered PLGA membranes for periodontal tissue regeneration. Dent. Mater. 34, 538-550, (2018).
You H., et al. Strong piezo-electrochemical effect of multiferroic BiFeO3 square micro-sheets for mechanocatalysis. Electrochem Commun. 2017;79:55-58.
Yu, J.; et al. Glucose-responsive insulin patch for the regulation of blood glucose in mice and minipigs. Nature Biomedical Engineering 2020, 1-8.
Yu, Y. et al. Multifunctions of dual Zn/Mg ion co-implanted titanium on osteogenesis, angiogenesis and bacteria inhibition for dental implants. Acta Biomater. 49, 590-603 (2017).
Zhang, H. et al. Drug delivery systems for differential release in combination therapy. Expert opinion on drug delivery 2011, 8, (2), 171-190.
Zhang, J. et al. Biodegradable Electrospun Poly (Lactic Acid) Nanofibers for Effective Pm 2.5 Removal. Macromolecular Materials and Engineering 2019, 304 (10), 1900259.
Zhang, Q.; et al. Transboundary Health Impacts of Transported Global Air Pollution and International Trade. Nature 2017, 543 (7647), 705-709.
Zhang, R. et al. Nanofiber Air Filters with High-Temperature Stability for Efficient Pm2. 5 Removal from the Pollution Sources. Nano letters 2016, 16 (6), 3642-3649.
Zhang, S.; et al. Spider-Web-Inspired Pm0. 3 Filters Based on Self-Sustained Electrostatic Nanostructured Networks. Advanced Materials 2020, 32 (29), 2002361.
Zhang, Y. et al. Preparation of Nanofibrous Metal-Organic Framework Filters for Efficient Air Pollution Control. Journal of the American Chemical Society 2016, 138 (18), 5785-5788.
Zhao et al., Electrospun poly(L-lactic acid) nanofibers for nanogenerator and diagnostic sensor applications. Macromol. Mater. Eng. 302, 1600476 (2017).
Zhou Y, Niu C, Ma B, Xue X, Li Z, Chen Z, Li F, Zhou S, Luo X, Hou Z: Inhibiting PSMalpha-induced neutrophil necroptosis protects mice with MRSA pneumonia by blocking the agr system. Cell Death Dis 2018, 9(3):362.
Zhu X, et al. Nanomedicine in the management of microbial infection—Overview and perspectives. Nano Today. 2014;9(4):478-498.

* cited by examiner

CORE-SHELL MICRONEEDLE PLATFORM FOR TRANSDERMAL AND PULSATILE DRUG/VACCINE DELIVERY AND METHOD OF MANUFACTURING THE SAME

CROSS-REFERENCE TO RELATED APPLICATIONS

This application is a divisional of U.S. patent application Ser. No. 16/293,588, filed on Mar. 5, 2019, which is a non-provisional of and claims the benefit of U.S. Provisional Patent Application No. 62/638,758, filed on Mar. 5, 2018, the contents of which are incorporated herein by reference.

BACKGROUND

Injections in conventional administration of vaccines are problematic. First, most of the vaccines are administered into children, who are needle-phobic. These painful injections could also cause infection and induce bad skin inflammatory reactions. Second and critically the injections require patients to memorize their vaccine schedules and bring their children to medical centers at multiple times. This is an immense obstacle for people who live in remote areas far away from medical centers. Millions of patients especially in developing countries currently have to walk tens of kilometers to bring their kids to medical centers multiple times when their children need vaccine shots. Therefore, patient accessibility is highly limited by the requirement of these multiple shots, leading to incomplete vaccination process, and the reoccurrence and spreading of deadly viral diseases. Third, in terms of cost, it is expensive to hire trained people/nurses to perform vaccine injections. Every year, about 10 million injections of vaccine are conducted for children under one year old (not including adults). As the price of administration is about $12/injection, it is about $120 million spent annually. This has not taken into account the waste of cold-chain vaccines (about $3 million a year per each state in the U.S.). The vaccine easily degrades during storage time between different shots and transportation processes. Finally, the injections produce millions of disposed sharp needles, producing a large amount of sharp hazardous biowaste. As such, these injections are a significant burden to patients, society, economics and environment. Consequently, there is a tremendous need to develop a single-administered painless and easy-to-use microneedle system with pulsatile release to replace conventional vaccine injections.

Microneedle patches have been explored and shown to exhibit advantages in transdermal delivery, however there have not been any reports on the use of this approach for single-administered multi-pulse delivery. Typically, current microneedles in which therapeutic agents are incorporated into the polymeric carriers only allow immediate or sustained releases. Another system like hollow microneedles even though provides a micro-infusing system, it requires an external drug reservoir on the skin or portable devices.

SEAL (StampED Assembly of polymer Layers) has demonstrated the concept of single-administered multi-pulse vaccine delivery. SEAL relies on a laborious manual process to remove scum/residual layers of polymer after molding steps and a slow process to fill drugs into polymeric carriers in serial (i.e., one by one). This filling struggles with instability of off-target jetting and severely suffers from the coffee-ring effect which results in drugs being deposited more on the edges of the drug micro-cores preventing a maximal loading efficiency (see FIG. 1).

SEAL has been shown to create different polymeric layers. However, the method results in a thick scum residual layer, requiring a manual, inconsistent and slow removal process (with scotch-tape and oxygen plasma). Using the so-called PRINT technology (Xu, J.; Wong, D. H.; Byrne, J. D.; Chen, K.; Bowerman, C.; DeSimone, J. M., Future of the particle replication in nonwetting templates (PR.INT) technology. Angewandte Chemie International Edition 2013, 52, (26), 6580-6589), researchers have shown that synthetic super-hydrophobic Teflon-like polymer can be employed to mold micro/nano particles without creating a scum layer. Yet, the polymer source is very limited and too costly while chemical synthesis is still required to obtain the final polymer resin.

Existing fabrication methods, although able to incorporate drugs with the microneedles, still struggle with major limitations. First, current fabrication methods have little-to-no control over microneedles internal structures to enable delayed pulsatile release. Due to such a limitation, available microneedles can only exhibit sustained release or immediately burst out drugs right after the needles are inserted into skin. Second, these microneedles are usually accompanied with a thick flashing/residual base layer, which potentially causes discomfort and skin irritation, making the needles not suitable for long-term skin integration.

SUMMARY

The core-shell microneedle system according to an embodiment provides a pulsatile drug delivery system which is programmed to release drugs/vaccines at predictable times using biodegradable polymers and with controllable dosages. This is the first microneedle system which would be fully embedded into the skin and then release drugs/vaccines as sharp bursts in a timely manner, similar to multiple bolus injections.

The fully-embedded coreshell microneedle is significantly less invasive compared to hypodermal/intramuscular injection of SEAL-particles. In terms of drug loading, the previous drug filling process is not only slow, laborious, and requires an expensive filling device but also struggles with instability of off-target jetting and severely suffers from the coffee-ring effect which results in drugs to be deposited more on the edges of the drug micro-cores, preventing a maximal loading efficiency (FIG. 1). Meanwhile, the new drug-loading and scum removing method do not suffer from such disadvantages and at the same time offer a high scalability The work includes two major innovations in terms of manufacturing technology and controlled-delivery drug-carrier. Although microneedle patches have been explored and shown to exhibit advantages in delivering and enhancing vaccine efficacy, there have not been any reports on the use of this approach for single-administered multi-pulse vaccine delivery. Herein, is disclosed novel core-shell microneedles which will be fully embedded into skin and release vaccines as sharp bursts in a predictable timely manner, similar to multiple bolus injections. The microneedles will not only allow for an easy, one-time self-administration of vaccine but also increase efficiency of the immunization since they target numerous antigen-presenting cells at the dermal layers. This is a tremendous benefit to solve the global problem of incomplete immunization while sparing antigen by boosting the vaccine activity.

Technology-wise, a highly innovative manufacturing process is disclosed that solves critical problems of the previously-reported SEAL method. (McHugh, K. J.; Nguyen, T.

D.; Linehan, A. R.; Yang, D.; Behrens, A. M.; Rose, S; Tochka, Z. L.; Tzeng, S. Y.; Norman, J. J.; Anselmo, A. C., Fabrication of Tillable microparticles and other complex 3D microstructures. Science 2017, 357, (6356), 1138-1142). Embodiments of the manufacturing method described herein eliminates the presence of scum/residual layer through a facile procedure. A new drug-loading approach, which does not rely on the serial and slow filling process, is also described. Arrays of molded drug cones are simultaneously placed into arrays of the microneedles in a parallel and high throughput manner while at the same time, sealing the drug cores.

The use of an advanced manufacturing technology to create novel core-shell microneedles, which could perform timely pulsatile release to solve the critical problem of repetitive and painful injections in conventional vaccine-administrations, makes this work innovative.

This new manufacturing process creates novel core-shell microneedles which can be fully inserted inside the skin and programmed to deliver vaccines or drugs at different times, similar to multiple bolus injections. These microneedles will increase patient accessibility to the vaccine, fostering the goal of global immunization to eradicate, and prevent deadly infectious diseases. Moreover, the needles would also offer a platform technology to administer versatile drugs (e.g., growth hormone, allergic drugs, pain medicine, etc.) which require frequent injections.

The ability to control internal structures and load different materials into cores of other materials allows us to create 3D micro-structures with an extreme complexity, while sustaining an excellent resolution and fidelity of the structures via micro-molding processes. Such 3D complexes of bioerodible polymers without any potentially-toxic impurities offer important applications in the fields of controlled drug delivery, tissue engineering and medical devices. The microneedle system disclosed herein can significantly enhance the efficiency of vaccine delivery by combining the concept of dermal/skin delivery and pulsatile release which has not been achieved from currently available microneedle patches.

In one embodiment, the disclosure describes a pulsatile drug delivery system comprising a microneedle assembly including a plurality of microneedles filled with a therapeutic agent. The microneedles comprise biodegradable polymers, and the microneedle assembly is configured to release the therapeutic agent at predetermined times with a predetermined amount of the therapeutic agent while the microneedle assembly remains embedded in a patient.

In another embodiment, the disclosure provides a method of manufacturing a microneedle assembly. The method comprises generating a core microneedle assembly by filling a first silicone mold including a plurality of microneedle cavities with a copolymer, spinning the first silicone mold to remove a first scum layer of the copolymer on the first silicone mold, and generating a core in each of the copolymer-filled cavities. The method further comprises generating a therapeutic agent assembly by filling a plurality of cavities in a second silicone mold with a therapeutic agent, spinning the second silicone mold to remove a second scum layer of the therapeutic agent, and removing the molded therapeutic agent from the second mold and transferring the molded therapeutic agent to a substrate. The method further comprises aligning the therapeutic agent assembly with the core microneedle assembly to thereby fill the cores in the core microneedle assembly with the therapeutic agent.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

A drug delivery system according to an embodiment of the present disclosure provides a one-time administration of one or more therapeutic agents of one or more dosages which are programmed to release at predictable time points. For example, degradation of the polymeric shell of the microneedles provides for release of the therapeutic agent. The drug delivery system can replace multiple bolus injections of many therapeutic agents, especially vaccines which require initial dose and multiple boosters.

The drug delivery system includes coreshell microneedles that overcome the above-noted SEAL limitations in fabrication, provide a minimally invasive approach, and allows for self-administration. Importantly, for vaccine delivery, the needles pierce into the dermis layer of the skin where there is a substantial number of immune cells, thereby significantly enhancing immune response. Microneedles are, therefore, an appealing delivery approach to enable one-time, painless, and effective administration of vaccines to replace multiple injections in the conventional immunization process. The microneedles are fabricated from FDA approved materials (e.g., Poly(D,L-lactide-co-glycolide) (PLGA), poly-lactide acid (PLA)) that are commonly used for drug delivery, medical devices, etc.

Figure 1:
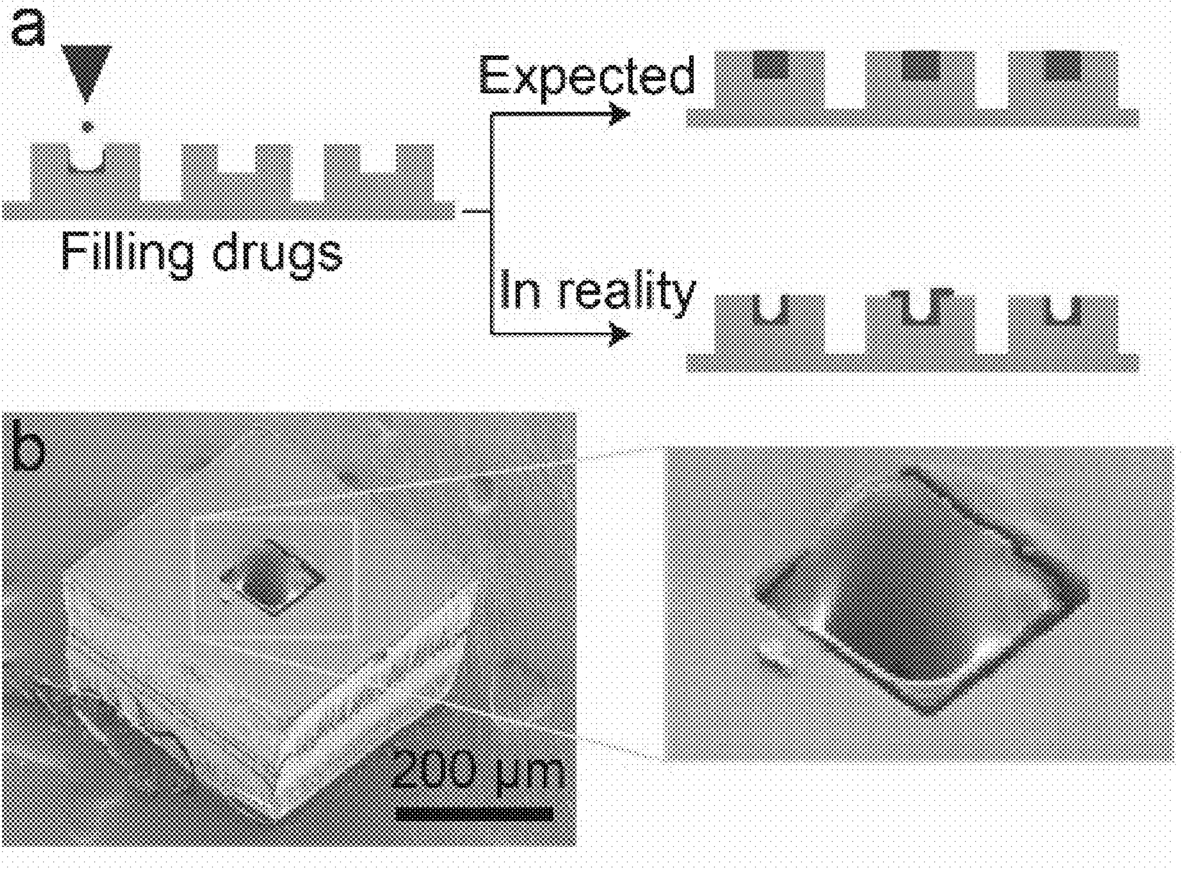
FIG. 1 illustrates current problems with the serial and slow filling process in SEAL. Schematic describes the problem (at a). Coffee-ring effect from solution-filling (at b).
Figure 2:
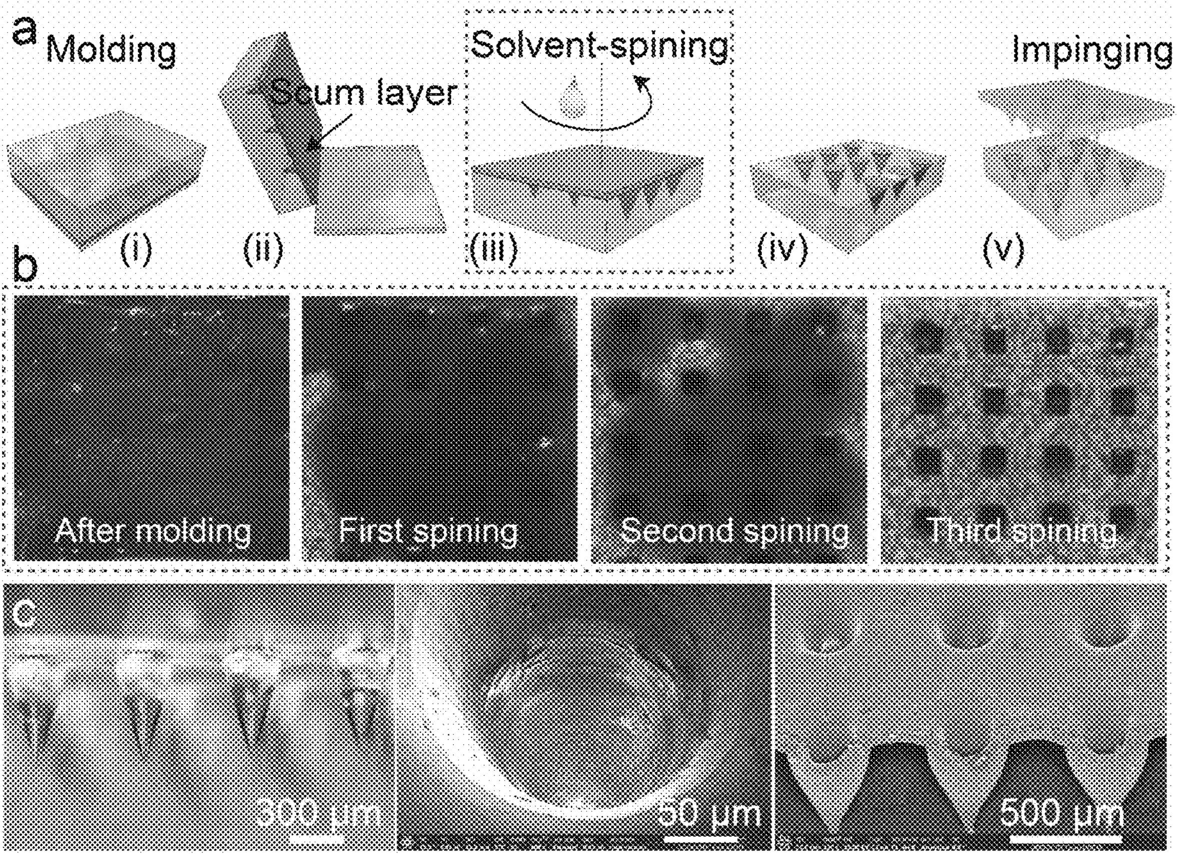
FIG. 2 illustrates fabrication of microneedles with empty cores (at a); optical images show step-by-step removal of scum layer by solvent-spinning (at b); and preliminary data on the fabricated microneedles with empty cores (at c).

The master structures for the microneedles are fabricated using a 3D laser lithography system (Nanoscribe GmbH). Inverse molds comprising silicone (Polydimethylsiloxane ("PDMS")) are made by pouring PDMS solution over the master structure and curing at 60° C. for 3 hours. A new process is employed which only relies on common PDMS molds to eliminate the scum layer. FIG. 2 (at a) describes the fabrication process in which a needle mold of PDMS is pressed onto a hot Poly(D,L-lactide-co-glycolide) ("PLGA") (i). The PLGA is trapped inside the cavity of the mold, which is then separated from the substrate (ii). The released mold has a significant scum layer which needs to be removed to create free-standing and fully-embeddable needles. To achieve this, the PDMS mold (using spin-coater) is spun and solvent (e.g., acetone, dimethyl sulfoxide ("DMSO")) or water (to remove hydrophilic drug) is gently dropped on top to remove the scum layer (iv). This spinning process can be repeated until the scum layer is completely removed.

FIG. 2 (at b) shows preliminary data in removing the scum layer of molded PLGA in PDMS. A high molecular weight PLGA (MW~200 kDa and LA:GA=85:15) is mixed with a red dye for visualization. This PLGA was molded into small slabs inside a PDMS mold. A thick scum layer was present after the molding process but after a few spinning steps with acetone, the scum layer was completely removed. In addition to scum layer removal, microneedles with conical empty cores were created by this impinging process, as seen in FIG. 2 (at c). In the final step (v), another mold is impinged onto the needle, trapped inside the PDMS mold, to create dimples or cores which are used to contain therapeutic agents.

Figure 3:
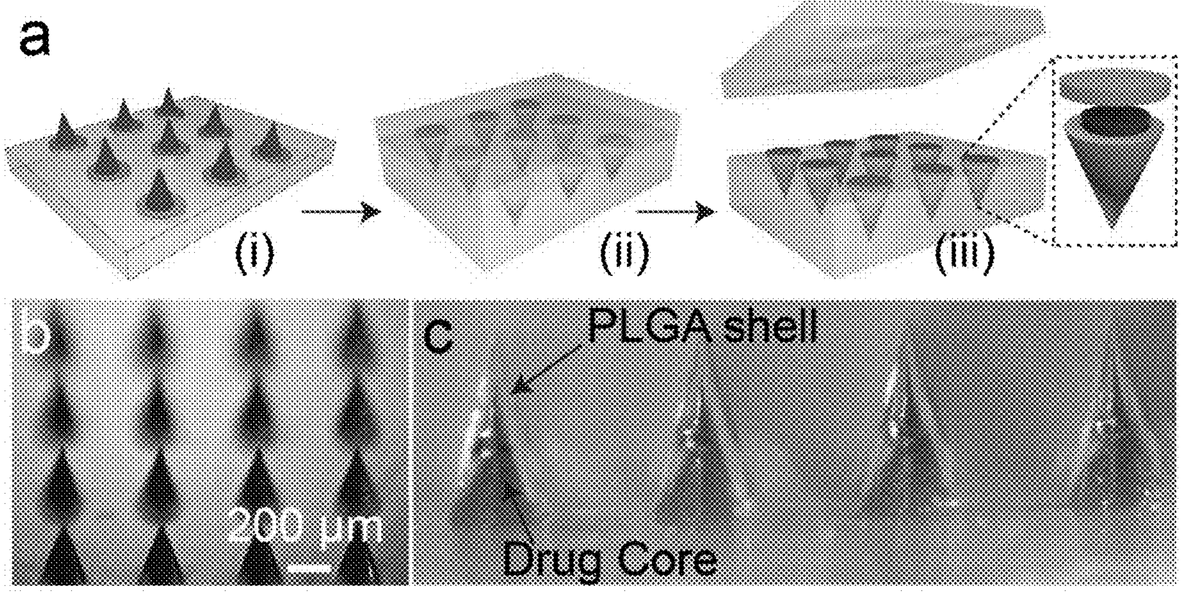
FIG. 3 illustrates microneedles being loaded and sealed with drugs in a single step. Diagram showing the process (at a). An image that shows micro-molded drug/vaccine cores with red dye and no scum-layer (at b). An image that shows preliminary data on the fabricated core-shell microneedles (at c).

SEAL relies on a slow and ineffective process to fill therapeutic agents into tiny micro-cores. Herein, a novel loading process to solve that problem is disclosed. First, a PDMS stamp is used to mold the drug/vaccine of interest into conical shapes, mixed with a polymeric carrier. Depending on the therapeutic agents, suitable polymeric solutions are selected. Some common polymers are Polyvinylpyrrolidone ("PVP"), Polyvinyl alcohol ("PVA"), Polyethylene glycol ("PEG"), (Hydroxypropyl)methyl cellulose ("HPMC"). Formulations can be made to improve the stability of drugs/vaccines. This disclosure demonstrates the use of PVP, the commonly used polymer for medical devices and implants such as wound dressings and drug tablets. The polymer is highly water-soluble, facilitating an immediate release of the encapsulated drugs with sharp release bursts after contact with water. The molding is similar to the process in FIG. 2 (at a, steps (i)-(ii)) but occurs at room/low temperatures to avoid damage to the vaccine. The scum layer is removed by spinning water on top of the PDMS stamp, containing the molded drug cones. The drug-PVP cores are then aligned and transferred on a cap-layer of PLGA, which has been molded and trapped inside another PDMS mold (see FIG. 3 (at a, (i)). Finally, this cap layer is aligned and pressed on the microneedle shell under a slightly-increased temperature to simultaneously load drugs and seal the microneedles, as seen in FIG. 3 (at a, (ii)-(iii)). The concentration of drugs in PVP can be easily tailored and the volume of the molded drug-core (FIG. 3 (at b)) can be approximated for one of the needle cores, allowing a maximal loading efficiency. The loading and sealing process was employed to successfully create the core-shell microneedles, as seen in FIG. 3 (at c). This process is further described with reference to FIGS. 5-6.

Figure 4:
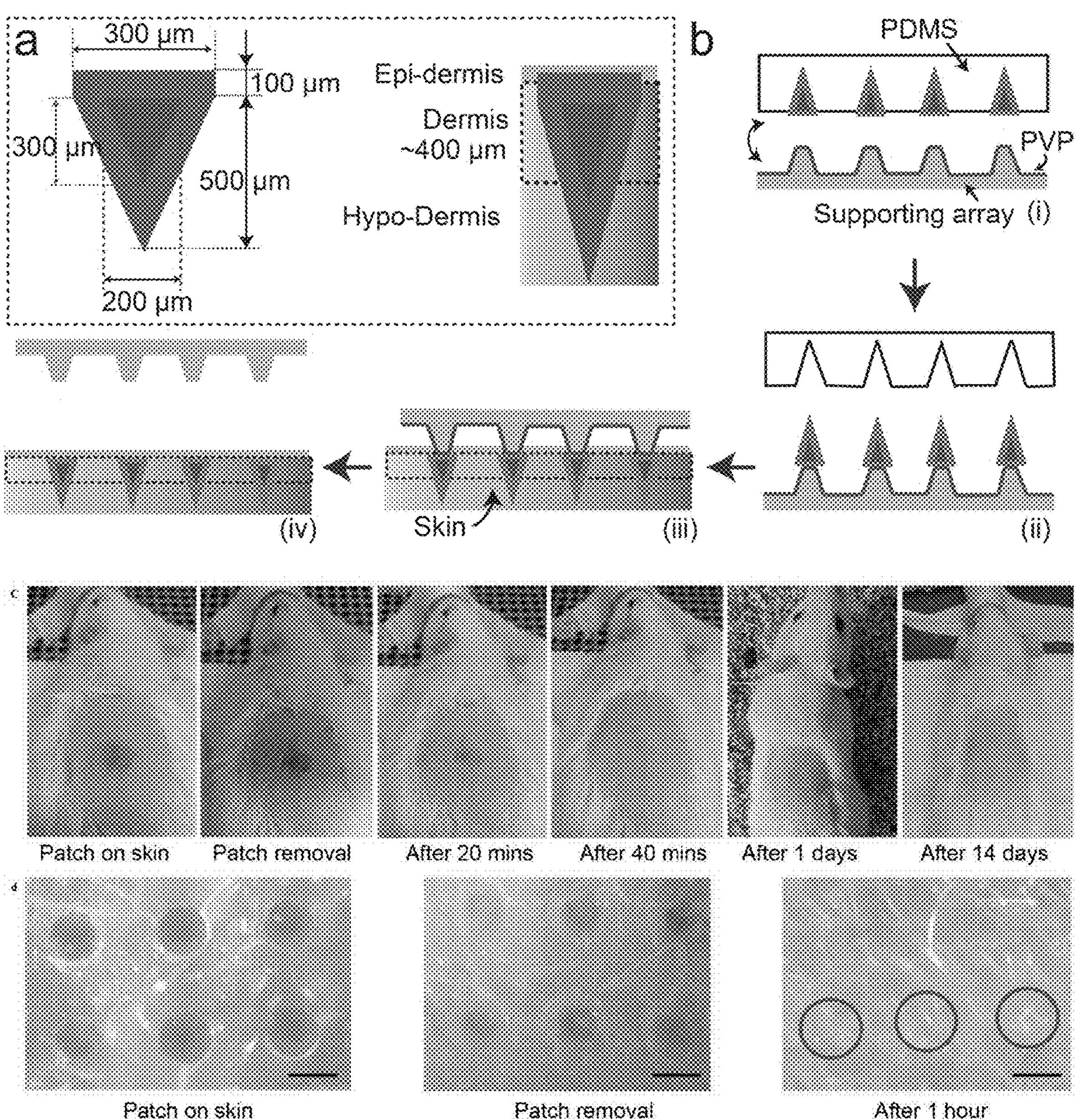
FIG. 4 illustrates a microneedle design and the use of supporting array to fully embed the needles into skin. Illustration showing exemplary dimensions of the microneedles (at a). Process to transfer microneedles onto a supporting array for insertion into skin (at b). Results (at c-d) show the fully-embedded microneedles inserted into rodent skin. The skin quickly heals after 60 minutes of implantation. The red circle shows the wound holes which are healed and closed up after 60 minutes of inserting/embedding the microneedles into the mice skin.

With reference to FIG. 4, in one embodiment, the drug core includes a maximum diameter of 200 μm and a height of 300 μm. This is short enough to allow the drug core to be situated inside the dermal layer of skin after insertion (FIG. 4 (at a, right)). The arrays made of PLA can be fabricated by micro-molding, without removal of the scum layer. PVP can be used to coat these arrays and selectively removed by water to release the drug microneedles into skin after insertion (FIG. 4 (at b, (iii)-(iv))). A PVP-coated PLA array is used as supporting arrays to fully implant the needles into skin. To bond the microneedles with the supporting array, the microneedles (trapped inside PDMS) can be aligned and brought into contact with the PLA supporting array and then a low heat can be applied for bonding (FIG. 4 (at b, (i)-(ii))). This process is again based on the SEAL method. As seen in FIG. 4 (at c), the fully-embedded microneedles are inserted into mice skin. The skin layer, after the needle insertion, could quickly heal to close up the opened wound/holes, as seen in FIG. 4 (at d).

Figure 5:
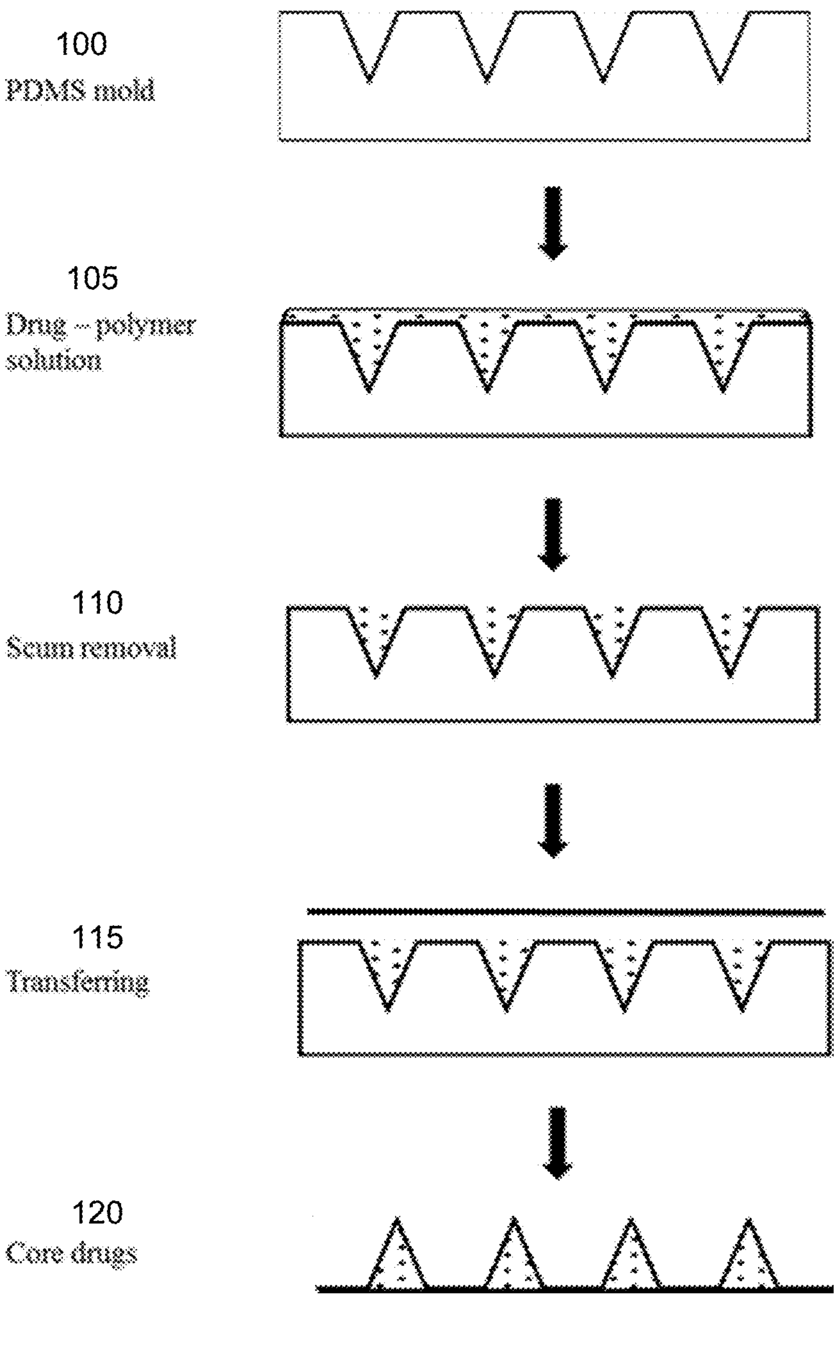
FIG. 5 illustrates a manufacturing process that generates a therapeutic agent assembly according to an embodiment of the invention.

With reference to FIG. 5, a manufacturing process that creates the drug delivery system according to an embodiment of the present disclosure is illustrated. In step 100, a non-adhesive negative mold (i.e., PDMS or Teflon, Polytetrafluoroethylene-PTFE or Perfluoropolyether-PFPE) is made by casting hydrophobic materials onto a master microneedles structure which is fabricated by photolithography or 3D printing or micro-machining etc. After the material is cured, it is peeled off from the master mold.

At step 105, to prepare the core-drugs, the therapeutic agents (e.g., drugs or vaccines such as Prevnar-13, HPV, IPV, insulin, growth hormone, pain medicine, allergic drugs, etc.) are dissolved or dispersed in suitable polymer solutions (i.e., water soluble polymer Poly(vinylpyrrolidone)—PVP or Poly(vinyl alcohol)—PVA).

Appropriate amounts of the solution or suspension are pipetted onto the prepared inverse mold as described above and left under vacuum to remove any air bubbles. Solvents are then allowed to evaporate. Lyophilization can be used to remove non-volatile organic solvents. Depending on the nature of solutions/suspensions, this step can be repeated several times and additional centrifugations can be applied until the mold is fully packed.

The above filling step usually results in a residual layer on the mold (scum layer). This scum layer is then removed as shown in step 110 by spinning accompanied with gently dropping of a suitable solvent (e.g., water, acetone, methanol, ethanol, dimethyl sulfoxide (DMSO)) on top of the mold. The chosen solvents should be able to dissolve the residual materials. The spinning speed depends on the viscosity of the materials and the architecture of the mold.

At step 115, the scum-free core-drugs are then transferred onto a sacrificial layer. The sacrificial layer can be a solid polymer film (i.e., PLGA) which is placed on top of the mold then compressed at its glass transition temperature under vacuum. Or, a concentrated polymer solution can be used as the sacrificial layer by pipetting onto the mold and allowing solvent to evaporate.

As shown in step 120, this whole structure is then delaminated onto a solid substrate, such as a glass slide, using heat-assisted micro-transfer molding. The fabricated core-drugs are used in a later loading step.

Figure 6:
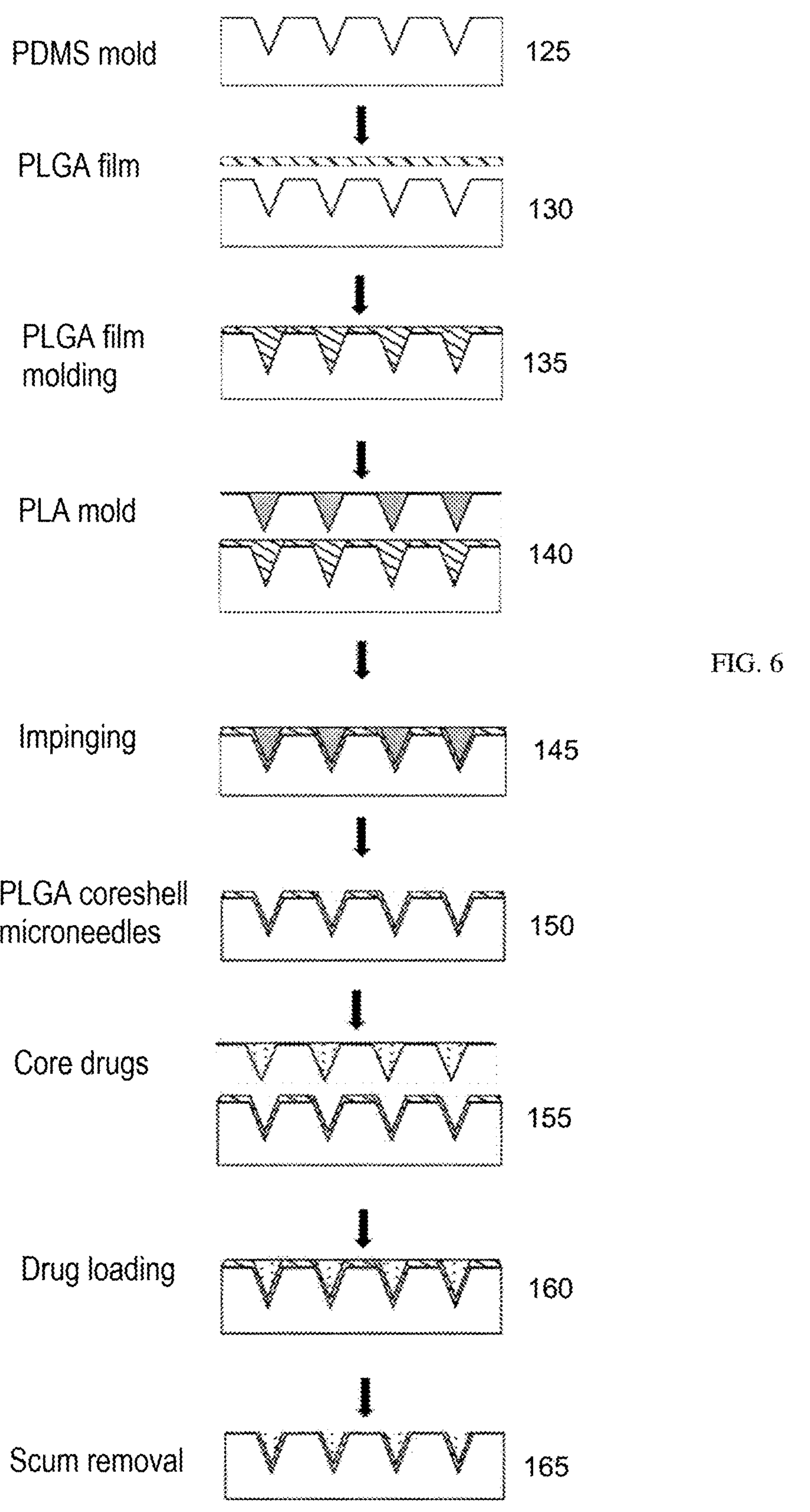
FIG. 6 illustrates a process of fabricating a core microneedle assembly and loading of a therapeutic agent according to an embodiment of the invention.

With reference to FIG. 6, a process of fabricating the coreshell microneedle and drug loading is illustrated. At step 125, a non-adhesive negative mold is made by casting hydrophobic materials (i.e., PDMS, Teflon, Polytetrafluoroethylene-PTFE, or Perfluoropolyether-PFPE) onto a master microneedles structure which is fabricated by photolithography, 3D printing, micro-machining, etc. After the material is cured, it is peeled off from the master mold.

A polymer film is then compression molded into the prepared mold at step 130 to form the microneedles. Typically, the polymer of interest such as PLGA is heat-pressed onto the mold at its melting or glass transition temperature under vacuum. The polymer fills the mold cavities at step 135.

To create the core structure, with reference to step 140, a positive mold which can be fabricated from polymers (e.g., PLA), metal, elastomers (PFPE), etc. is first prepared by compression molding, micro-machining, photolithography. Depending on the hydrophobicity of the materials, additional surface treatment can be applied to the mold in order to prevent adhesion in later manufacturing steps.

At step 145, this core structure or second mold which has smaller dimensions and the same relative spacing is aligned, using an alignment device, and then pressed into the microneedles (on the PDMS mold) which have been heated prior to this step. At an elevated temperature, the second mold will penetrate into the soft microneedles, creating dimple-like structures in the microneedles.

At step 150, after peeling off the second mold, the coreshell microneedles are obtained and trapped inside the first mold.

At step 155, the core-drugs are aligned using a similar device as above and loaded into the coreshell microneedles.

The residual scum layer is then removed at step 160 using the same method as described above. Suitable solvents are dropped onto the mold while spinning at high speed. At step 165, the scum-free coreshell microneedles are entrapped inside the mold.

Figure 7:
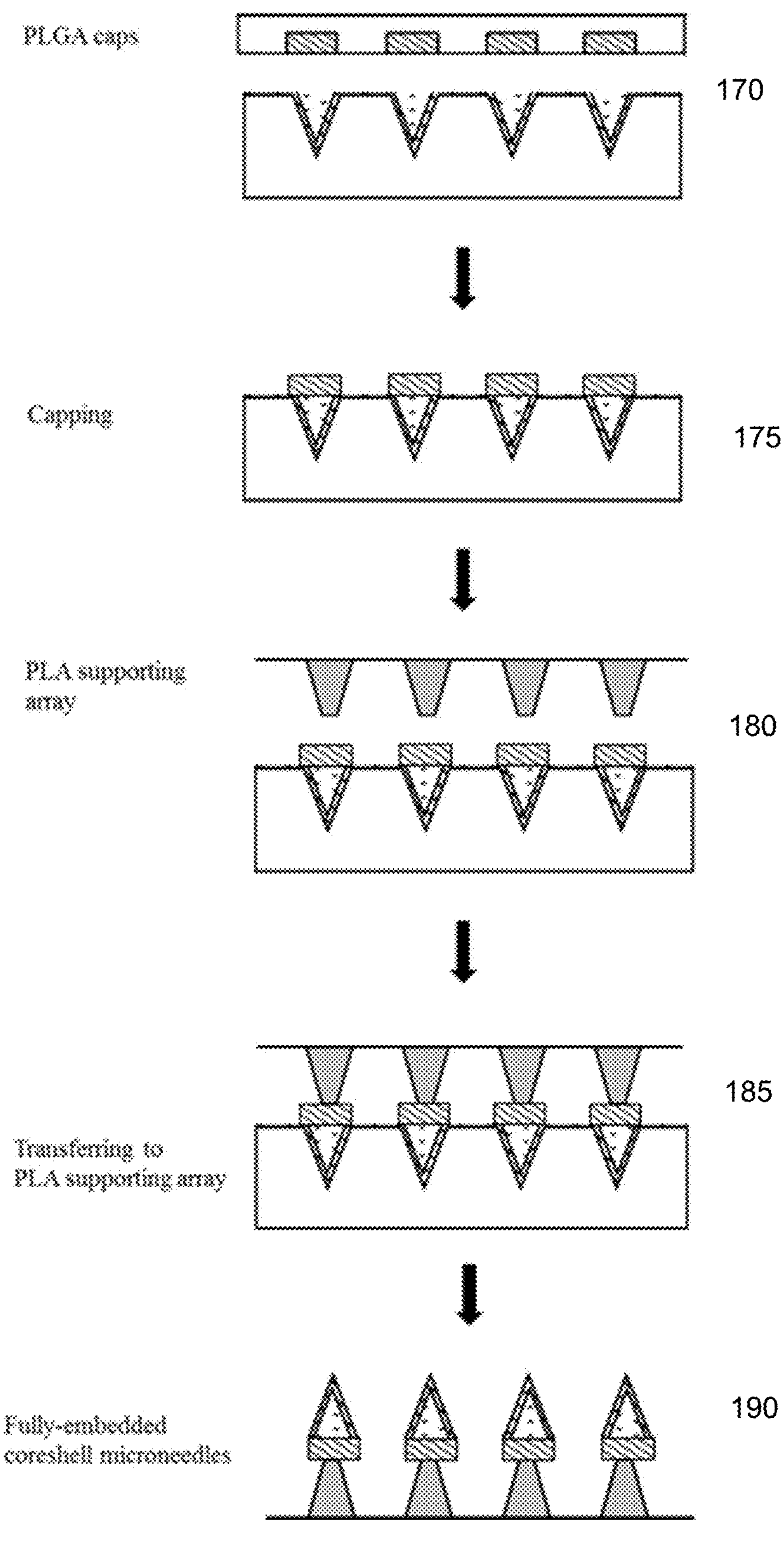
FIG. 7 illustrates a method for fabricating caps for the core microneedle assembly according to an embodiment of the invention.

With reference to FIG. 7, which is a continuation of FIG. 6, caps for the coreshell microneedles are fabricated by following similar procedures of compression molding and scum removal. In brief, another mold for the caps is made by a similar casting of hydrophobic materials on a master structure as described above. A polymer film such as PLGA is compression molded into the mold under heating and vacuum at step 170. Then the scum layer is removed leaving individual caps.

At step 175, the caps trapped inside the mold are aligned and placed on top of the fabricated coreshell microneedles from FIG. 6. With heat-assistance, the caps are bonded with the coreshell microneedles base. The mold is then peeled off.

In the next step, step 180, the coreshell microneedles are transferred onto a supporting array. This array can be manufactured by several microfabrication methods like compression molding, micro-machining, or photolithography.

The array is then coated at step 185 with a water soluble polymer (i.e., PVP, PVA). Then, it is aligned with the coreshell microneedles, contact between them is made, and sufficient heat for bonding with the PLGA caps is supplied.

The mold entrapping the coreshell microneedles is then peeled off at step 190 leaving a free standing coreshell microneedle assembly on the supporting array which can be fully-embedded into the skin.

The drug delivery system may include a computer processor in electronic communication with the coreshell microneedle assembly. The computer processor is programmed with computer readable instructions to initiate active release of the therapeutic agent either as a one-time release or as a plurality of pre-programmed timed releases of the therapeutic agent. The computer processor can be in electronic communication with an actuator (e.g., piezoelectric (mechanical) pump, electromagnetic pump, or electrical pump can be integrated into the microneedle patch) to initiate the release of the therapeutic agent into the skin based on the programmed instructions.

Various features and advantages of the invention are set forth in the following claims.

What is claimed is:

1. A drug delivery system comprising:
an assembly including
a substrate, and
a plurality of microneedles extending from the substrate, each microneedle including:
a shell including a biodegradable polymer, said shell having a tapered shape from a distal tip to a proximal base having a diameter larger than the distal tip,
a core including a mixture of a therapeutic agent and a polymeric carrier,
and
a cap including a biodegradable polymer, the cap bonded to the base of the shell and enclosing the core within the shell, said cap and shell not including any therapeutic agent, and
said assembly comprising:
a water-soluble polymer layer between the cap and the substrate, said water-soluble polymer layer connecting the microneedles to the substrate with the tips of the microneedles directed away from the substrate,
wherein the water-soluble polymer layer is configured to dissolve to release the microneedles from the substrate when the microneedles are inserted into the skin of a patient, leaving the microneedles embedded in the skin where the cap and shell of each of the plurality of microneedles degrade at a predetermined time to release the therapeutic agent therein into the skin of the patient.

2. The drug delivery system of claim 1, wherein the biodegradable polymer of the shell includes Poly(D,L-lactide-co-glycolide) ("PLGA") or poly-lactide acid ("PLA").

3. The drug delivery system of claim 2, wherein the cap includes PLGA or PLA.

4. The drug delivery system of claim 1, wherein the polymeric carrier is Polyvinylpyrrolidone, Polyvinyl alcohol, Polyethylene glycol, or (Hydroxypropyl)methyl cellulose.

5. The drug delivery system of claim 1, wherein the cap and shell of a first subset of the plurality of microneedles is selected to degrade at a first time to release the therapeutic agent therein into skin of a patient, and wherein the cap and shell of a second subset of the plurality of microneedles is selected to degrade at a second time different from the first time to release the therapeutic agent therein into the skin of the patient.

6. The drug delivery system of claim 1, wherein the therapeutic agent is a vaccine.

7. The drug delivery system of claim 6, wherein the cap and shell of a first subset of the plurality of microneedles is selected to degrade at a first time to release a first dose of the vaccine therein into skin of a patient, and wherein the cap and shell of a second subset of the plurality of microneedles is selected to degrade at a second time different from said first time to release a second dose of the vaccine therein into the skin of the patient.

8. The drug delivery system of claim 1, wherein the therapeutic agent is insulin or a growth hormone.

9. The drug delivery system of claim 1, wherein the therapeutic agent treats pain or allergy symptoms of a patient.

10. The drug delivery system of claim 1, wherein the core of at least one of the microneedles includes a maximum diameter of 200 μm and a maximum height of 300 μm.

11. The drug delivery system of claim 10, wherein at least one of the microneedles in the plurality of microneedles includes a maximum height of 600 μm.

* * * * *